(12) United States Patent
Richmond et al.

(10) Patent No.: US 10,512,512 B2
(45) Date of Patent: Dec. 24, 2019

(54) SYSTEM AND METHOD FOR TISSUE CONTACT DETECTION AND FOR AUTO-EXPOSURE AND ILLUMINATION CONTROL

(71) Applicant: INTUITIVE SURGICAL OPERATIONS, INC., Sunnyvale, CA (US)

(72) Inventors: Geoff Richmond, San Jose, CA (US); Brian D. Hoffman, Mountain View, CA (US); Jeffrey M. DiCarlo, Austin, TX (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 346 days.

(21) Appl. No.: 15/126,960

(22) PCT Filed: Mar. 17, 2015

(86) PCT No.: PCT/US2015/020892
§ 371 (c)(1),
(2) Date: Sep. 16, 2016

(87) PCT Pub. No.: WO2015/142799
PCT Pub. Date: Sep. 24, 2015

(65) Prior Publication Data
US 2017/0095297 A1 Apr. 6, 2017

Related U.S. Application Data

(60) Provisional application No. 61/954,336, filed on Mar. 17, 2014, provisional application No. 61/954,381, filed on Mar. 17, 2014.

(51) Int. Cl.
*A61B 1/00* (2006.01)
*A61B 1/045* (2006.01)
(Continued)

(52) U.S. Cl.
CPC .......... *A61B 34/30* (2016.02); *A61B 1/00006* (2013.01); *A61B 1/00009* (2013.01);
(Continued)

(58) Field of Classification Search
CPC ..... A61B 34/30; A61B 90/30; A61B 1/00006; A61B 1/00009; A61B 1/00062;
(Continued)

(56) References Cited

U.S. PATENT DOCUMENTS 6,080,104 A * 6/2000 Ozawa ................. H04N 5/2351
348/69
6,464,633 B1 * 10/2002 Hosoda ................ A61B 1/0638
348/68
(Continued)

FOREIGN PATENT DOCUMENTS

| EP | 2682044 A1 | 1/2014 |
|---|---|---|
| EP | 2749202 A1 | 7/2014 |

(Continued)

OTHER PUBLICATIONS

International Preliminary Report on Patentability for Application No. PCT/US15/20892, dated Sep. 29, 2016, 8 pages.
(Continued)

*Primary Examiner* — Timothy J Neal
*Assistant Examiner* — William B Chou

(57) ABSTRACT

Scenes captured with an endoscope (201) of a teleoperated surgical system (200) and displayed on a display unit (251) maintain a consistent brightness even though optical output power of an illuminator (210) changes, and working distance (204) between tissue (203) and the distal tip of the endoscope changes. Teleoperated surgical system (200) also automatically detects when endoscope (201) contacts tissue (203) and adjusts the output optical power of illuminator (210) so that tissue damage does not occur.

18 Claims, 10 Drawing Sheets

(51) Int. Cl.
*A61B 1/06* (2006.01)
*A61B 34/30* (2016.01)
*A61B 90/30* (2016.01)
*A61B 90/00* (2016.01)

(52) U.S. Cl.
CPC ...... *A61B 1/00062* (2013.01); *A61B 1/00165* (2013.01); *A61B 1/00193* (2013.01); *A61B 1/045* (2013.01); *A61B 1/06* (2013.01); *A61B 90/30* (2016.02); *A61B 2034/301* (2016.02); *A61B 2090/065* (2016.02); *A61B 2090/0801* (2016.02); *A61B 2090/08021* (2016.02)

(58) Field of Classification Search
CPC . A61B 1/00165; A61B 1/00193; A61B 1/045; A61B 1/06
USPC ........ 600/109, 113, 117, 118, 160, 178, 179, 600/180, 181, 182
See application file for complete search history.

(56) References Cited

U.S. PATENT DOCUMENTS

| | | | |
|---|---|---|---|
| 6,511,422 | B1 | 1/2003 | Chatenever |
| 7,070,560 | B2 * | 7/2006 | Takahashi .............. A61B 1/045 362/574 |
| 8,878,920 | B2 * | 11/2014 | Ovod ...................... A61B 1/06 348/68 |
| 9,709,794 | B2 * | 7/2017 | Weiger ............... G02B 23/2423 |
| 2001/0056238 | A1 | 12/2001 | Tsujita |
| 2003/0078477 | A1 | 4/2003 | Kang et al. |
| 2007/0276198 | A1 | 11/2007 | Eli |
| 2008/0239070 | A1 | 10/2008 | Westwick et al. |
| 2009/0118578 | A1 | 5/2009 | Takasugi et al. |
| 2014/0046341 | A1 | 2/2014 | DiCarlo |
| 2014/0092226 | A1 | 4/2014 | Kuriyama et al. |

FOREIGN PATENT DOCUMENTS

| | | |
|---|---|---|
| JP | H10192232 A | 7/1998 |
| JP | 2000056240 A | 2/2000 |
| JP | 2002078670 A | 3/2002 |
| JP | 2002085345 A | 3/2002 |
| JP | 2002282207 A | 10/2002 |
| JP | 2006055503 A | 3/2006 |
| JP | 2007195850 A | 8/2007 |
| JP | 2012065690 A | 4/2012 |
| JP | 2012085790 A | 5/2012 |
| JP | 2013042998 A | 3/2013 |
| WO | WO-2012127469 A1 | 9/2012 |
| WO | WO-2013027455 A1 | 2/2013 |

OTHER PUBLICATIONS

International Search Report and Written Opinion for Application No. PCT/US15/20892, dated Jun. 8, 2015, 11 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Extended European Search Report for Application No. EP15764341. 2, dated Nov. 13, 2017, 8 pages.

* cited by examiner

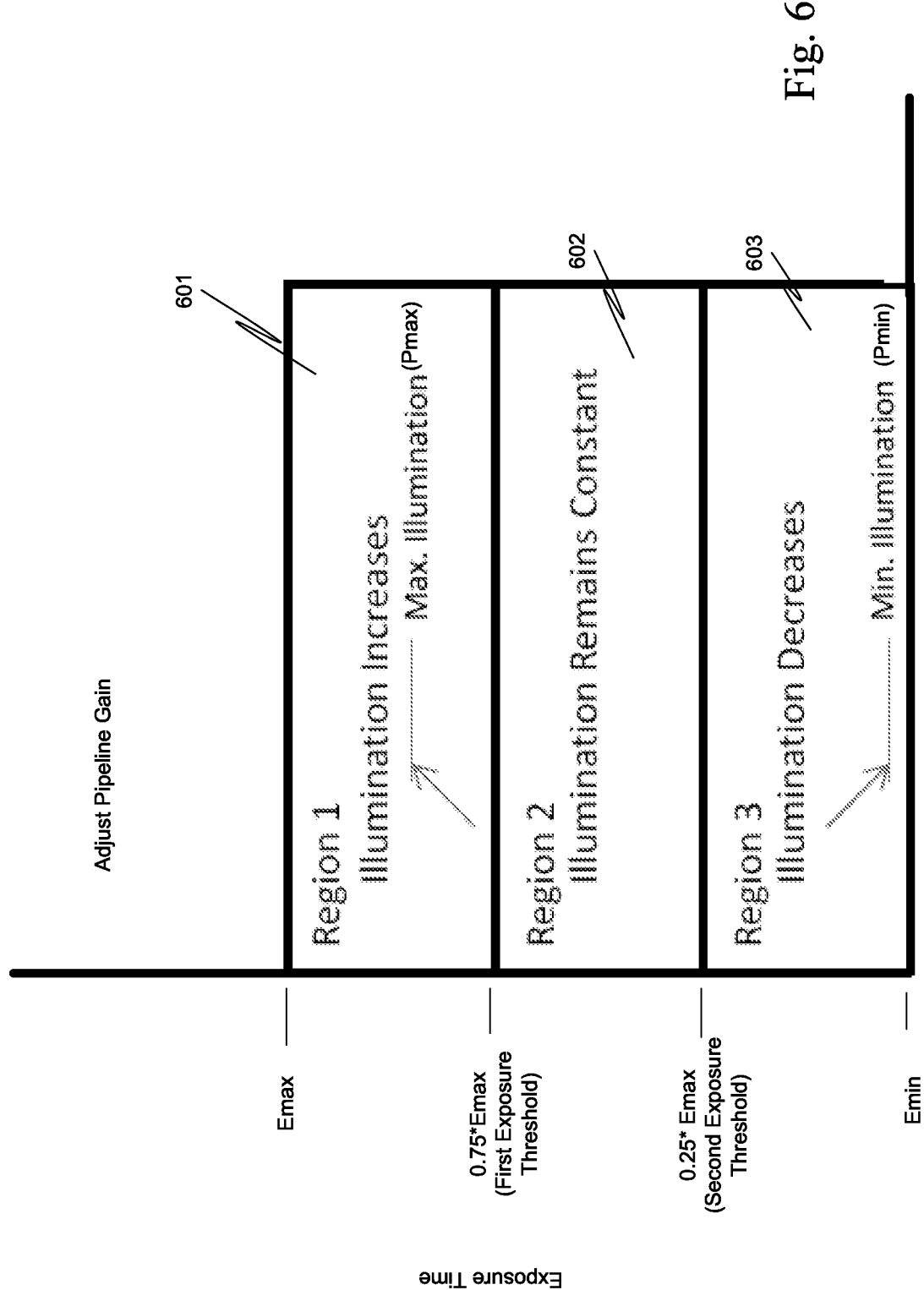

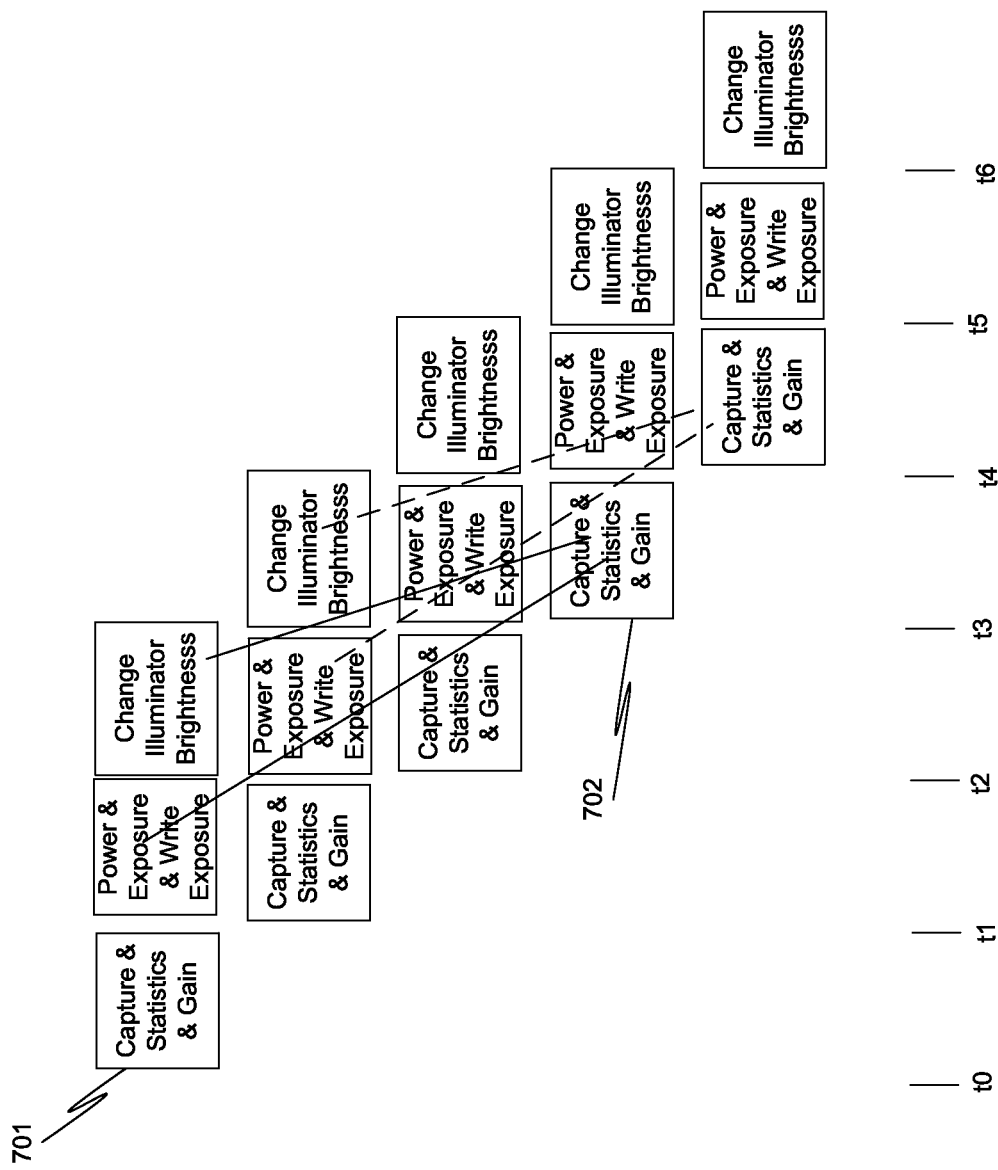

SYSTEM AND METHOD FOR TISSUE CONTACT DETECTION AND FOR AUTO-EXPOSURE AND ILLUMINATION CONTROL

RELATED APPLICATIONS

This application is the U.S. national phase of International Application No. PCT/US2015/020892, filed Mar. 17, 2015, which designated the U.S. and claims priority to U.S. provisional patent application 61/954,336, filed on Mar. 17, 2014, and to U.S. provisional patent application 61/954,381, filed on Mar. 17, 2014, the contents of each of which are incorporated herein by reference.

BACKGROUND

Field of Invention

Aspects of this invention are related to endoscopic imaging and are more particularly related to tissue contact detection, displayed scene brightness control, camera auto-exposure control, and illumination control in a teleoperated surgical system.

Related Art

The da Vinci® Surgical System, commercialized by Intuitive Surgical, Inc., Sunnyvale, Calif., is a minimally invasive teleoperated surgical system that offers patients many benefits, such as reduced trauma to the body, faster recovery and shorter hospital stay. One feature of the da Vinci® Surgical System is a capability to provide two-channel (i.e., left and right) video capture and display of visible images to provide stereoscopic viewing for the surgeon. Such electronic stereoscopic imaging systems may output high definition video images to the surgeon, and may allow features such as zoom to provide a "magnified" view that allows the surgeon to identify specific tissue types and characteristics, as well as to work with increased precision.

However, the illumination of a surgical site and the exposure time of a camera used during capture of an image of a surgical site are some of the factors affecting the quality of the images provided to the surgeon. For example, U.S. Pat. No. 8,512,232 B2 describes introducing into a body an endoscope that provides a first level of illumination and also introducing into the body an illumination apparatus that provides a second level of illumination. The second level of illumination is greater than the first level of illumination and is used for imaging a large target area. The lower level of illumination from the endoscope is used for imaging a smaller target area.

However, a potential problem with a high intensity light source has been recognized and a solution provided in U.S. Pat. No. 6,511,422 B1. According to this patent, the output from a high intensity light source is controlled so that whenever the output is not directed at tissue, the light source output intensity is automatically reduced to a safe level. The light reflected from tissue is monitored and if the reflected light indicates that the light source is not directed at tissue, the light intensity is turned down to a safe level.

SUMMARY

In a teleoperated surgical system, if a controller detects contact of an endoscope tip with tissue, the controller attenuates output optical power from the endoscope tip. This ensures the tissue is not damaged as a result of the contact.

In one aspect, the controller detects the contact by monitoring reflected luminance from tissue and by monitoring the output optical power from the endoscope. The controller determines that contact occurred if a change from a first output optical power to a second output optical power does not result in a change of reflected luminance for the second output optical power compared to a reflected luminance for the first output optical power.

The controller varies the output optical power from the endoscope tip in a known pattern following the attenuating. The controller detects whether reflected luminance changes with the varying output optical power. If the reflected luminance follows the known pattern of the varying output optical power, the controller terminates the attenuating.

A teleoperated surgical system includes an illuminator, a camera, and a controller. The illuminator provides output optical power. The camera is configured to capture a scene including tissue. The controller is coupled to the illuminator and to the camera. The controller is configured to detect contact of an endoscope with tissue. The controller is configured to attenuate the output optical power following contact being detected.

The controller includes a statistics module coupled to the camera. The statistics module receives the scene captured by the camera. The statistics module generates a brightness histogram for the captured scene and determines an overall brightness of the captured scene. A contact detection module in the controller is coupled to the statistics module. The contact detection module receives the overall brightness of the captured scene and receives a camera exposure time. The contact detection module is also coupled to the illuminator. The contact detection module detects contact of the tip of the endoscope with tissue.

In one aspect, the illuminator includes a dither module. The dither module is coupled to the contact detection module. The dither module is configured to vary the output optical power in a known pattern following being enabled by the contract detection module. An auto-exposure module is coupled to the statistics module. The auto-exposure module is configured to detect brightness changes in captured scenes.

A teleoperated surgical system includes a control system. The control system includes a camera control unit and an illumination controller. The illumination controller is configured to control output optical power from an illuminator of the teleoperated surgical system. The camera control unit is configured to receive a video stream from a camera of the teleoperated surgical system. The camera control unit is coupled to the illumination controller. The camera control unit also is configured to command the illumination controller to change the output optical power from a first output optical power to a second output optical power, and is configured to command the camera to change the camera exposure time from a first exposure time to a second exposure time so that a frame is subsequently captured with the second exposure time from light reflected from the second output optical power.

In one aspect, a light source is coupled to the illumination controller. An endoscope is coupled to the light source. A camera is coupled to the endoscope and is coupled to the camera control unit.

In one aspect, the camera control unit includes a statistics module. The statistics module is coupled to the camera to receive the video stream. The statistics module is configured to create a brightness histogram for a frame in the video stream. The camera control unit also includes an auto-exposure module coupled to statistics module. The auto-exposure module is configured to maintain a target brightness of a displayed scene, the displayed scene being a scene from a captured frame. Also, the auto-exposure module is configured to limit saturated pixels in scenes of captured frames to less than a predetermined number of pixels in each of the scenes. In addition, the auto-exposure module is configured to maintain a minimum output optical power from the illuminator.

In another aspect, the camera control unit includes first and second control loops. The first control loop is configured to automatically adjust one or both of a video pipeline gain and a camera exposure time so that the displayed scene has the target brightness.

The second control loop is configured to automatically adjust the output optical power and to adjust the camera exposure time for a subsequently captured frame. The second control loop is configured to adjust the output optical power and the camera exposure time based on a value of the camera exposure time.

The second control loop increases the output optical power and decreases the camera exposure time if the camera exposure time is larger than a first exposure threshold. The second control loop decreases the output optical power and increases the camera exposure time if the camera exposure time is smaller than a second exposure threshold. The second control loop leaves the output optical power and the camera exposure time unchanged if the camera exposure time is between the first exposure threshold and the second exposure threshold.

In one aspect, the first control loop and the second control loop are included in an auto-exposure module. A statistics module is coupled to the camera to receive the video stream and is coupled to the auto-exposure module. The statistics module is configured to create a brightness histogram for a frame in the video stream.

In one aspect, the camera control unit includes a control loop configured to automatically adjust a target brightness of a displayed scene to reduce a number of saturated pixels in a subsequently captured frame. The control loop is configured to apply a range-constrained reduction to the target brightness.

In still another aspect, the camera control unit includes an auto-exposure module. The auto-exposure module is coupled to the statistics module to receive the brightness histogram for a frame in the video stream. Also, the auto-exposure module is configured to determine an average brightness using the information in the histogram. The auto-exposure module is also configured to adjust one or both of a video pipeline gain and the camera exposure time based on a relation of the average brightness to the target brightness. The auto-exposure module also reduces the target brightness when a number of saturated pixels in a captured scene is larger than a saturated pixel threshold. In addition, the auto-exposure module is configured to command the illumination controller to change a first illuminator output to a second illuminator output and to command the camera to adjust the camera exposure to compensate for the change in illuminator output.

A method of operating a teleoperated surgical system includes adjusting one or both of a video pipeline gain and a camera exposure time using an average brightness of a captured scene and a target brightness for a displayed scene. The method also configures output optical power of an illuminator and exposure time of a camera using the camera exposure time. The method reduces a number of saturated pixels in a second captured frame by reducing the target brightness.

BRIEF DESCRIPTION OF THE DRAWINGS

FIG. 6 is a diagram illustrating output optical power control using camera exposure time.

FIG. 7 is a pipeline diagram for the camera control unit of FIG. 2 and the process flow diagram of FIG. 4.

Figure 1A:
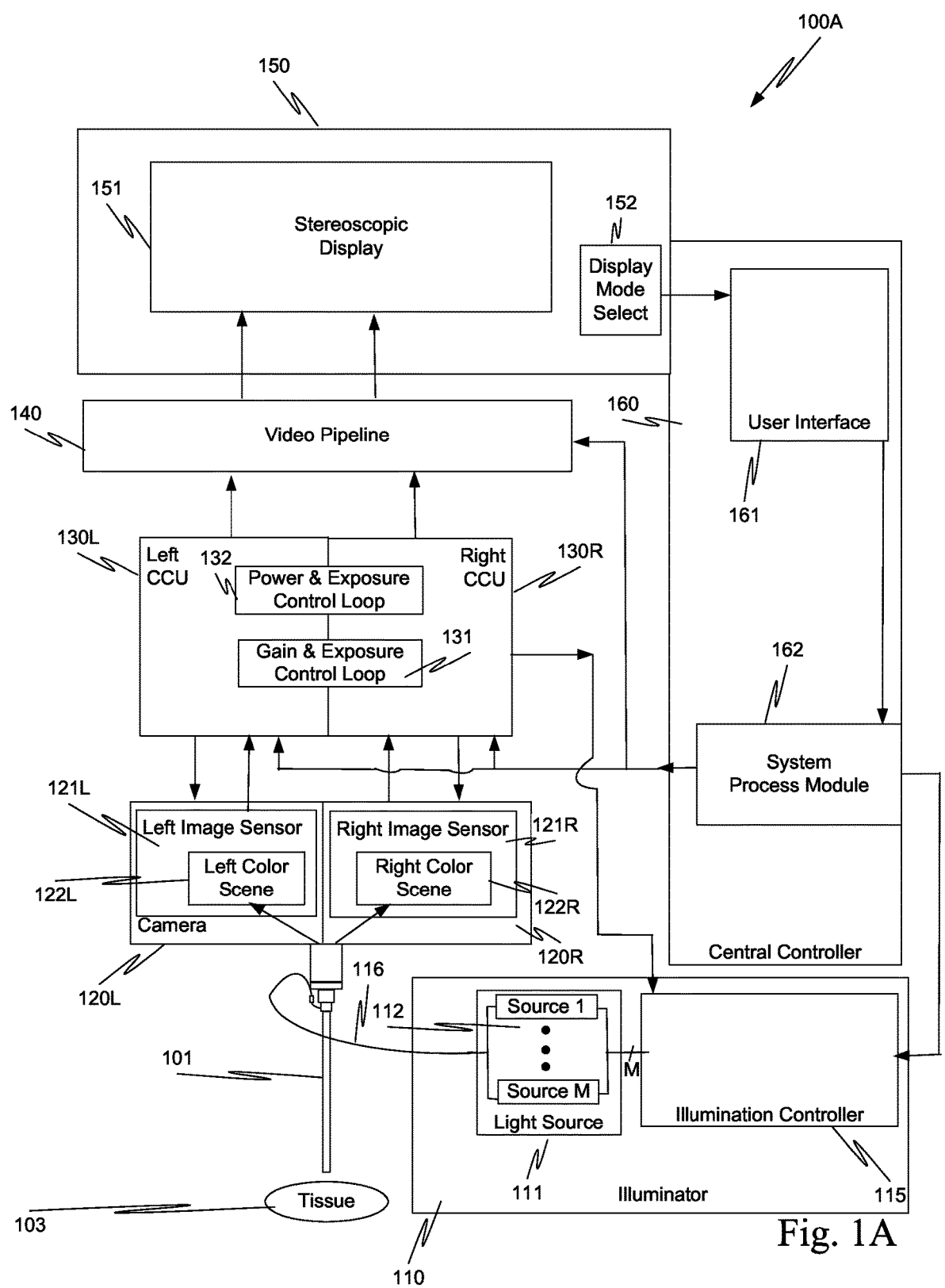
FIGS. 1A and 1B are block diagrams of a teleoperated surgical systems that include a controller for controlling some or all of a number of saturated pixels in a scene, for controlling a video pipeline gain, for controlling an output optical power, for controlling a camera exposure time, and for detecting tissue contact.

In the drawings, the first digit of a reference number indicates the figure in which the element with that reference number first appeared.

DETAILED DESCRIPTION

In one aspect, scenes captured with endoscope 101 of teleoperated surgical systems 100A and 100B (FIGS. 1A and 1B) and displayed on stereoscopic display unit 151 maintain a consistent brightness even though the working distance between tissue 103 and the distal tip of endoscope 101 changes. Teleoperated surgical systems 100A and 100B also automatically detect when endoscope 101 contacts tissue and adjusts the output optical power of illuminator 110 so that tissue damage does not occur.

Illumination having an output optical power, e.g., visible light, from an illuminator 110 exits endoscope 101 at a distal tip of endoscope 101, sometimes referred as a tip. The illumination is reflected from tissue 103 and is captured as frame 122L that includes a left color scene captured by left image sensor 121L of left camera 120L and as a frame 122R that includes a right color scene captured by right image sensor 121R of right camera 120R. Each of left and right image sensors 121L and 121R is said to capture a frame that includes a scene.

The captured frames are passed frame by frame as a video stream to camera control units 130L and 130R where each frame is processed and then to passed to video pipeline 140. Video pipeline 140 processes each frame in a manner equivalent to the processing of video pipelines in prior teleoperated surgical systems, except as described below, and then passes the frame to stereoscopic display 151 in a surgeon's console 150.

Thus, tissue 103 is viewed by the user of teleoperated surgical systems 100A and 100B on surgeon's console 150. While a video sequence of scenes are displayed on stereoscopic display 151, the scenes appear to the user as a continuous image of tissue 103, e.g., the user sees tissue 103 move, sees bleeding, sees motion due to breathing, etc. However, the user will notice changes in brightness in the scenes displayed on stereoscopic display 151, which can be distracting. Teleoperated surgical system 100 maintains a consistent brightness of the displayed scenes even though the working distance between tissue 103 and the distal tip of endoscope 101 changes, either increases or decreases. While in this example, a stereoscopic endoscope is used, systems 100A and 100B work the same for an endoscope having a single optical channel by processing a single captured scene.

The scenes displayed on stereoscopic display 151 have a predetermined brightness, which is referred to as a target brightness. In one aspect, the target brightness is set by teleoperated surgical systems 100A and 100B. However, in some aspects, a surgeon is permitted to adjust the target brightness so that the brightness of the displayed scenes is acceptable to the surgeon.

In one aspect, an endoscopic control system includes a controller that in turn includes camera control units 130L and 130R and an illumination controller 115. In one aspect, camera control units 130L and 130R include two control loops 131, 132. (FIG. 1A) The combination of control loops 131 and 132 is configured to maintain a target brightness of a displayed scene (the displayed scene being a scene in a captured frame) and is configured to maintain a minimum illuminator output.

As endoscope 101 moves away from tissue 103, if gain and exposure control loop 131 detects a decrease in overall brightness of a scene captured by left image sensor 121L and a scene captured by right image sensor 121R, gain and exposure control loop 131 automatically either commands cameras 120L, 120R to increase the camera exposure time so that subsequently captured images have the target brightness or commands video pipeline 140 to increase the gain that controls the brightness of the scene displayed on display unit 151 so that the displayed scene has the target brightness. In some situations, gain and exposure control loop 131 automatically commands both an increase in the camera exposure time and an increase in the video pipeline gain. Power and exposure control loop 132 determines whether the output optical power from illuminator 110 should be increased. If the output optical power is increased, power and exposure control loop 132 increases the output optical power of illuminator 110 and decreases the exposure time of cameras 120L and 120R frame by frame in fixed-size synchronized linear steps.

The increase in output optical power and the decrease in exposure time are the same size change, e.g., if the increase in output optical power is one percent, the decrease in exposure time is one percent. If the system were perfect, there would be no change in overall brightness of a scene captured with the output optical power and new exposure time relative to the scene captured with the original output optical power and original exposure time. However, since systems are not perfect, there may be a change in overall brightness of a scene captured with the new output optical power and new exposure time. Thus, the fixed size of the steps is selected so that any flicker in the brightness of the displayed images caused by the synchronized changes of output optical power and exposure time is not noticed by the surgeon.

Similarly, as endoscope 101 moves toward tissue 103, if gain and exposure control loop 131 detects an increase in the brightness of scenes captured by left image sensor 121L of left camera 120L and by right image sensor 121R of right camera 120R, gain and exposure control loop 131 automatically either commands cameras 120L, 120R to decrease the camera exposure time so that subsequently captured images have the target brightness or commands video pipeline 140 to decrease the gain that controls the brightness of the scene displayed on display unit 151 so that the displayed scene has the target brightness. In some situations, gain and exposure control loop 131 automatically commands both a decrease in the camera exposure time and a decrease in the video pipeline gain. Power and exposure control loop 132 determines whether the output optical power from illuminator 110 should be decreased. If the output optical power should be decreased, power and exposure control loop 132 decreases the output optical power of illuminator 110 and increases the exposure time of cameras 120L and 120R frame by frame in the fixed-size synchronized linear steps. However, if the decrease in output optical power reaches a minimum output optical power, the output optical power of illuminator 110 is maintained at the minimum output optical power.

In another aspect, camera control units 130L and 130R include three control loops 131, 132, 133. (FIG. 1B) The combination of control loops 131, 132, and 133 is configured to maintain a target brightness of a displayed scene (the displayed scene being a scene in a captured frame), is configured to limit saturated pixels in scenes of captured frames to less than a predetermined number of pixels in each of the scenes, and is configured to maintain a minimum illuminator output. In this aspect, control loops 131 and 132 function in the same way as described above.

In addition to changes in brightness, which can be distracting to surgeons, any region of a displayed scene that fails to convey the details of the region can distract a surgeon. Image sensors 121L and 121R capture light in wells referred to as pixels. Each well has a limited capacity and if too much light is captured by a well, the well overflows and so contains no useful information. When a well overflows, the pixel is referred to a saturated pixel.

If a region of tissue 103 reflects so much light that the pixels capturing light reflected by that region of tissue are saturated, the surgeon sees the region on stereoscopic display 151 as a bright spot with no details. Any information about the nature of the tissue, blood vessels in the region, etc. is lost. Thus, in one aspect, saturated pixels control loop 133 determines a number of saturated pixels in an entire frame and if the number of saturated pixels is large enough to be distracting to a surgeon, saturated pixels control loop 133 reduces the target brightness in fixed-size linear steps frame by frame until the number of saturated pixels in a frame is smaller than the number that would be distracting to a surgeon. However, the decrease in target brightness is range limited. This means that the target brightness can be reduced no more than a fixed percentage of the original target brightness that was set by the system or selected by the surgeon, e.g., the maximum change in target brightness is limited to less than thirty-five percent of the original target brightness. Thus, saturated pixels control loop 133 is configured to apply a range-constrained reduction to the target brightness.

Since saturated pixels control loop 133 analyzes the total number of saturated pixels in the entire frame, the operation of the saturated pixels control loop 133 is not dependent on the location of the saturated pixels in the frame. This approach maintains a consistent displayed brightness of the scenes as the locations of features causing the saturated pixels change in the displayed scenes, e.g., as a surgical instrument moves about in the scene.

If endoscope 101 (FIGS. 1A and 1B) continues to move toward tissue 103, eventually endoscope 101 contacts tissue 103. The contact is observed by detecting a change in output optical power level that results in little or no change in reflected luminance from tissue 103. When this situation is detected by camera control units 130L and 130R, the output optical power of illuminator 110 is reduced to a level that is safe for tissue contact.

There are situations other than tissue contact where a change in output optical power results in little or no change in the reflected luminance from tissue 103, e.g., the distal tip of endoscope 101 is withdrawn into a cannula. To prevent such false positives from inhibiting the operation of endoscope 101, while the output optical power of illuminator 101 is at the level that is safe for tissue contact, the output optical power is varied in a known way. If this known variation in the output optical power is detected by camera control units 130L and 130R, endoscope 101 is not in contact with tissue and normal control of the output optical power is resumed by camera control units 130L and 130R.

Thus, in one aspect, a controller detects contact of an endoscope tip with tissue by monitoring the reflected luminance from tissues 103 and by monitoring the output optical power. The controller attenuates output optical power from the endoscope tip upon detecting the contact. Since the reflected luminance is not measured directly, the controller determines the reflected luminance as the ratio of the overall brightness of a captured scene to the camera exposure time. Here, the overall brightness is taken as the average brightness of the frame.

Hence, to detect the contact, the controller monitors the reflected luminance, i.e., a ratio of the overall brightness of a captured scene to the camera exposure time, and monitors output optical power from endoscope 101. The controller determines that the endoscope tip contacted the tissue if a change from a first output optical power to a second output optical power does not result in a change in the ratio compared to the ratio for a scene captured from light reflected from the first output optical power, i.e., does not result in a change in the reflected luminance.

One example of a teleoperated surgical system 100 (FIGS. 1A and 1B) is the da Vinci® minimally invasive teleoperated surgical system commercialized by Intuitive Surgical, Inc. of Sunnyvale, Calif. Teleoperated surgical systems 100A and 100B are illustrative only and are not intended to be limiting. In this example, a surgeon at surgeon's console 150 remotely manipulates endoscope 101 mounted on a robotic manipulator arm (not shown). There are other parts, cables, etc. associated with the da Vinci® Surgical System, but these are not illustrated in FIGS. 1A and 1B to avoid detracting from the disclosure. Further information regarding teleoperated minimally invasive surgical systems may be found for example in U.S. patent application Ser. No. 11/762,165 (filed Jun. 13, 2007; disclosing Minimally Invasive Surgical System) and U.S. Pat. No. 6,331,181 (filed Dec. 18, 2001; disclosing Surgical Robotic Tools, Data Architecture, and Use), both of which are incorporated herein by reference.

An illumination system, e.g., illuminator 110, is coupled to endoscope 101. In one aspect, illuminator 110 includes a light source 111 and an illumination controller 115. Illumination controller 115 is coupled to light source 111 and to camera control units 130L, 130R.

In the aspect of FIG. 1, light source 111 includes a plurality of color component illumination sources 112. In one aspect, plurality of color component illumination sources 112 includes a plurality of light emitting diodes (LEDs). The use of LEDs is illustrative only and is not intended to be limiting. Plurality of color component illumination sources 112 could also be implemented with multiple laser sources or multiple laser diodes instead of LEDs, for example. Alternatively, light source 111 could use a Xenon lamp with an elliptic back reflector and a band pass filter coating to create broadband white illumination light for visible images. The use of a Xenon lamp also is illustrative only and is not intended to be limiting. For example, a high-pressure mercury arc lamp, other arc lamps, or other broadband light sources may be used.

In this aspect, illuminator 110 is used in conjunction with at least one illumination path in stereoscopic endoscope 101 to illuminate tissue 103. Output light from illuminator 110 is directed into a connector 116. Connector 116 provides the light to an illumination path in stereoscopic endoscope 101 that in turn directs the light to surgical site 103. Each of connector 116 and the illumination path in stereoscopic endoscope 101 can be implemented, for example, with a fiber optic bundle, a single stiff or flexible rod, or an optical fiber. Endoscope 101 also includes, in one aspect, two optical channels, i.e., a stereoscopic optical path, for passing light reflected from surgical site 103 to cameras 120L, 120R.

Camera 120L is coupled to a stereoscopic display 151 in surgeon's console 150 by a left camera control unit 130L and video pipeline 140. Camera 120R is coupled to stereoscopic display 151 in surgeon's console 150 by a right camera control unit 130R and video pipeline 140. Camera control units 130L, 130R receive signals from a system process 162. System process 162 and central controller 160 represents some of the various controllers in system 100.

Display mode select switch 152 provides a signal to a user interface 161 that in turn passes the selected display mode to system process 162, e.g., a high power mode. Various controllers within system process 162 configure illumination controller 115, configure left and right camera control units 130L and 130R to acquire the desired images, and configure any other elements in video pipeline 140 needed to process the acquired images so that the surgeon is presented the requested images in display 150. Video pipeline 140 is equivalent to known video pipelines, except for the details provided herein.

Although described as central controller 160, it is to be appreciated that central controller 160 as well as each of the other controllers described herein may be implemented in practice by any number of modules and each module may include any combination of components. Each module and each component may include hardware, software that is executed on a processor, and firmware, or any combination of the three. Also, the functions and acts of central controller 160 and each of the other controllers, as described herein, may be performed by one module, or divided up among different modules or even among different components of a module. When divided up among different modules or components, the modules or components may be centralized in one location or distributed across systems 100A and 100B for distributed processing purposes. Thus, central controller 160 and each of the other controllers described herein should not be interpreted as requiring a single physical entity, as in some aspects the controllers may be distributed across systems 100A and 100B.

Figure 1B:
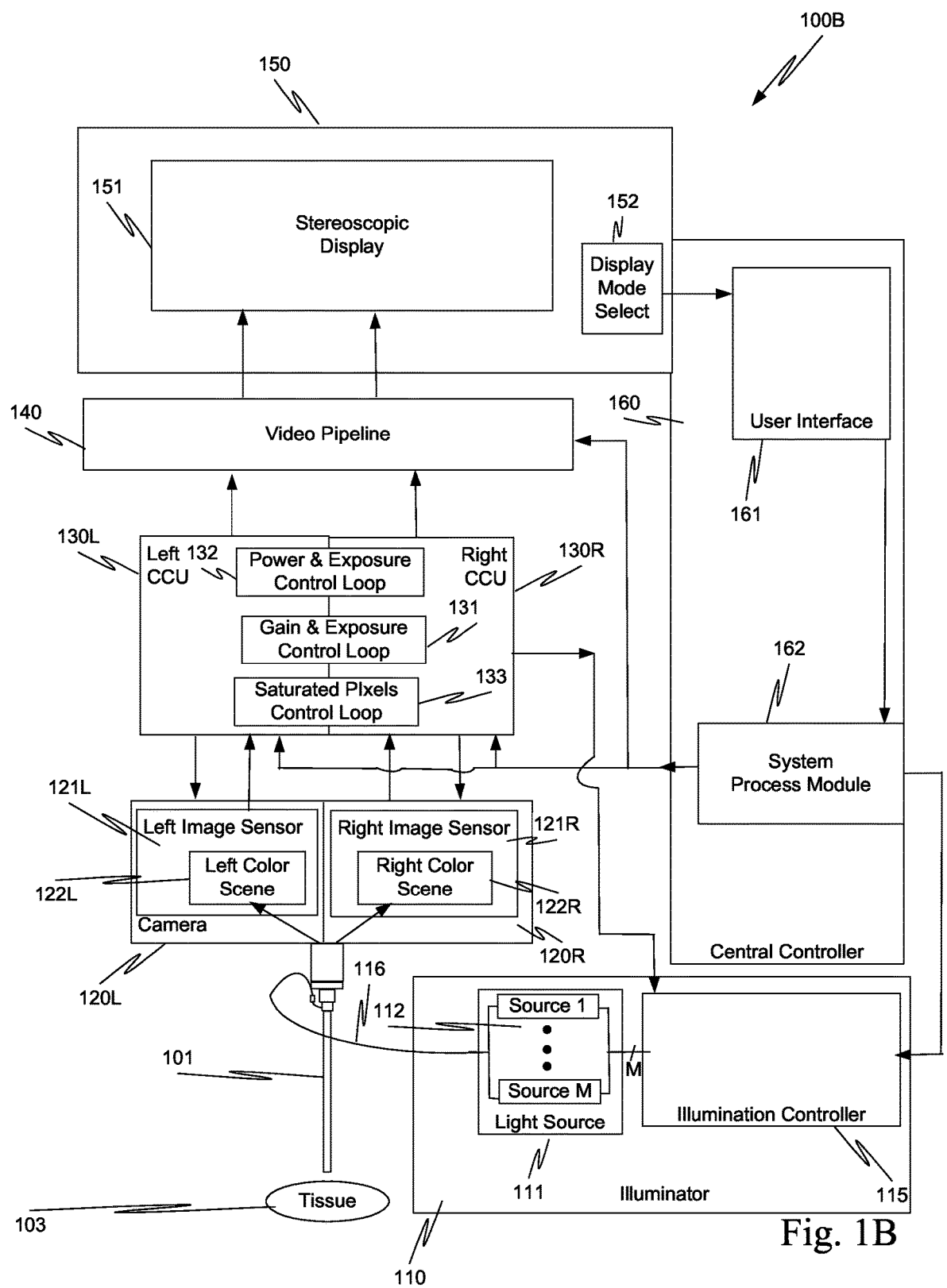
Figure 2:
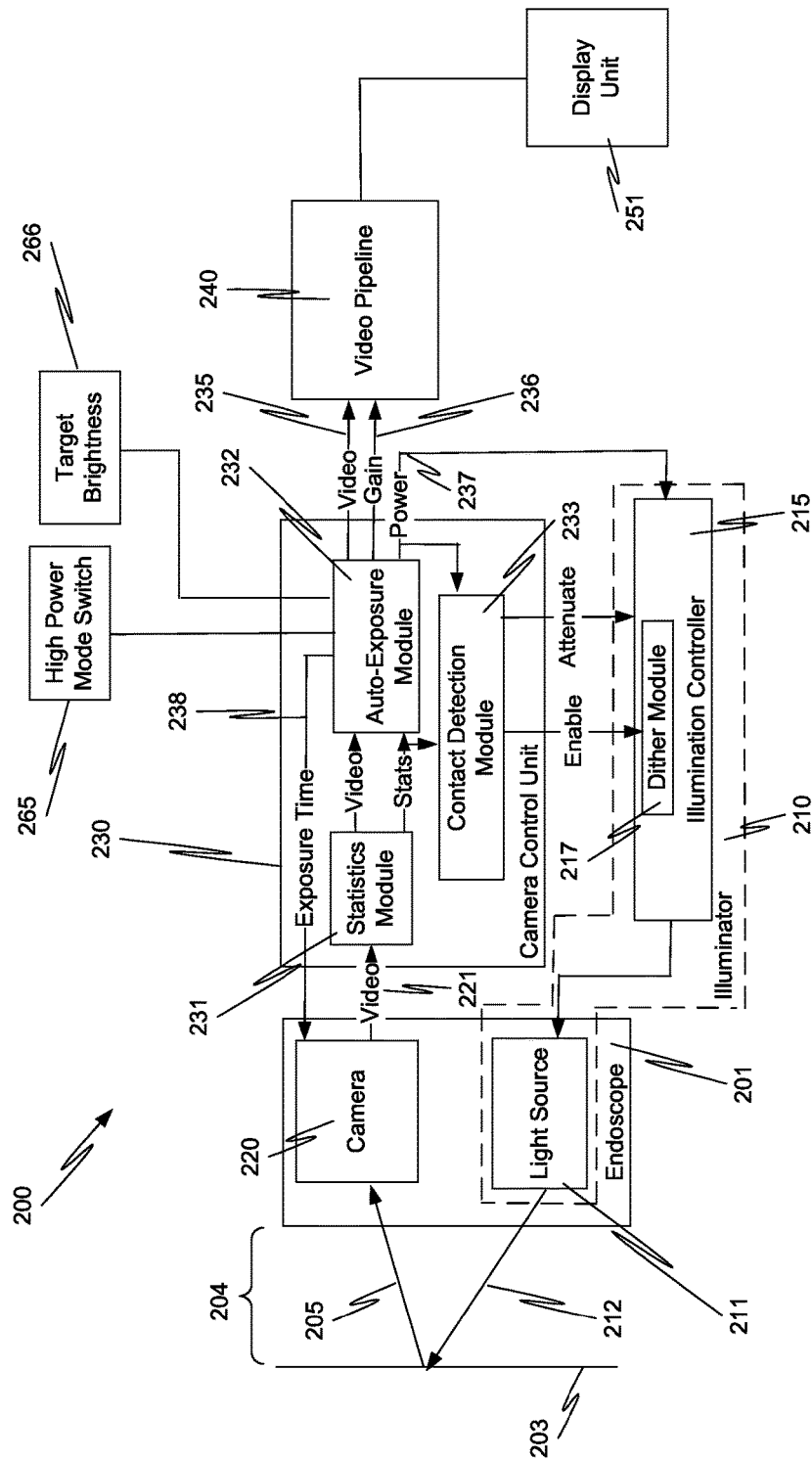
FIG. 2 is another block diagram of teleoperated surgical system that includes a controller for controlling a number of saturated pixels in a scene, for controlling a video pipeline gain, for controlling an output optical power, for controlling a camera exposure time, and for detecting tissue contact.

In FIGS. 1A and 1B, cameras 120L, 120R and light source 112 are shown as being external to endoscope 101. However, in one aspect, cameras 120L, 120R and light source 112 are included in the distal tip of endoscope 101. For example, in FIG. 2, camera 220 and light source 211 are included in endoscope 201 of teleoperated surgical system 200.

Again, one example of a teleoperated surgical system 200 is the da Vinci® minimally invasive teleoperated surgical system discussed above. Teleoperated surgical system 200 is illustrative only and is not intended to be limiting. As with teleoperated surgical systems 100A and 100B, there are other parts, cables, etc. associated with the da Vinci® Surgical System, but these are not illustrated in FIG. 2 to avoid detracting from the disclosure.

In this example, a controller also includes camera control unit 230 and illumination controller 215. In one aspect, camera control unit 230 represents camera control units 130L and 130R and camera 220 represents cameras 120L and 120R. In another aspect, camera control unit 230 is coupled to a single optical channel in camera 220.

Camera control unit 230 includes an auto-exposure module 232 that controls the brightness of scenes displayed on display unit 251. In addition, output optical power control by illumination controller 215 is also tied into auto-exposure module 232 to provide automatic illuminator dimming when the surgical scenario does not require maximum output optical power or automatic illuminator brightening when the surgical scenario requires more illumination than a minimum output optical power. In clinical applications, it is desirable to use only as much light as necessary to provide good quality video. This avoids any negative tissue interaction due to higher power illumination.

Light from light source 211 that is reflected by target 203, e.g., a surgical site, is captured as a color scene by camera 220. Light source 211 has an output optical power 212 that is controlled by illumination controller 215 in response to commands from auto-exposure module 232 and in response to commands form contact detection module 233. Target 203 has a luminance 205, which is an indication of the brightness of target 203. Normally, as output optical power 212 increases or decreases luminance 205 of target 203 increases or decreases. To avoid confusion with the luminance of a captured image, the luminance of target 203 is referred to as "reflected luminance," and luminance of a captured image is referred to as "captured image luminance" or "image luminance."

In one aspect, camera 220 is a rolling shutter camera. As used here, a rolling shutter means that instead of reading the entire frame from the image sensor of the camera at once, information is read from each row of the frame one after the other, top to bottom.

Camera 220 captures a continuing sequence of frames that comprises a video stream. Each captured frame includes a color scene that is a snapshot of target 203 at an instant in time. Video 221 is streamed from camera 220 to a statistics module 231 in camera control unit 230. Statistics module 231 collects real-time statistics about each frame in the video stream. These statistics include a histogram of pixel brightness of the frame, which is fed to auto-exposure module 232. As explained more completely below, auto-exposure module 232 controls the target brightness, the exposure time of camera 220, the gain in video pipeline 240, and the output optical power from endoscope 201. In one aspect, auto-exposure module 232 is configured to:
  maintain a target brightness of the video image displayed on display unit 251;
  maintain a total number of saturated pixels in each scene captured by camera 220 below a saturated pixel threshold; and
  maintain a minimum output optical power (minimum illumination brightness) necessary to achieve the target brightness for scenes captured by camera 220.

In another aspect, auto-exposure module 232 is configured to:
  maintain a target brightness of the video image displayed on display unit 251; and
  maintain a minimum output optical power (minimum illumination brightness) necessary to achieve the target brightness for scenes captured by camera 220.

As used herein, a target brightness is a brightness of scenes displayed on display unit 251. An initial target brightness, sometimes referred to as the original target brightness, is set in teleoperated surgical system 200, e.g., a target brightness of 1500. However, in one aspect, a slide switch is presented in a user interface presented on display unit 251, which permits the user to select a target brightness for the displayed scenes that is acceptable for the user. The initial target brightness was empirically determined based on feedback from users of teleoperated surgical systems such as the da Vinci teleoperated surgical system. The target brightness is a control parameter in control loops within auto-exposure module 232, as explained more completely below.

As explained more completely below, auto-exposure module 232 ensures a constant brightness of the displayed scene in a frame by ensuring the average brightness of the scene is equal to the target brightness. Herein, the mean or average brightness of a scene is referred to as the overall brightness of the scene or the overall brightness of the frame. Auto-exposure module 232 also limits the effect of saturated pixels in the displayed scene by applying a range-constrained reduction to the target brightness. Auto-exposure module 232 controls the output optical power of illuminator 210 using a brightness threshold with hysteresis.

As explained more completely below, the control system implemented by auto-exposure module 232 controls the video pipeline gain 236 and camera exposure time 238. In the absence of saturated pixels, the change in overall brightness of the captured scene is a linear function of video pipeline gain 236 and camera exposure time 238.

However, any saturated pixels in a scene are inherently non-linear. Unfortunately, very bright specular highlights combined with a limited bit-depth or limited dynamic range of camera 220 and/or video pipeline 240 result in saturation of pixels in the scene displayed on display unit 251. Also, saturated pixels are undesirable in the image, because detail is lost in the region of the saturated pixels.

Specular highlights are created from anatomy that is highly reflective and are created from metallic (highly reflective) instruments travelling through the field-of-view of endoscope 201. Auto-exposure module 232 is configured to minimize scene brightness changes as instruments move throughout the scene and to minimize the user-adjustment of any auto-exposure parameters.

One method of minimizing the effect of a reflective instrument moving throughout the scene is to use spatial information available in teleoperated surgical system 200 about the most-likely location of the instruments and to focus the auto-exposure on areas of the scene where instruments are not likely to be located. One approach is to define a rectangular region in the center of the scene. In this case statistics module 231 would generate image statistics only for pixel locations in the rectangular region. This allows the instruments to move in the periphery of the scene, without affecting the brightness of the displayed scene. This approach might be useful for surgical procedures and teleoperated surgical systems where the instruments do not have a large range of motion and so do not frequently move through the rectangular region.

However, if the instruments have a large range of movement and so move through the rectangular region, use of statistics for only the rectangular region produces an invisible barrier (the outline of the region), where, if a reflective instrument crossed this barrier, a dramatic change of scene brightness would occur, because auto-exposure module 232 would adjust for increased brightness in the region due to reflections from the highly reflective instrument. The changes in brightness associated with instruments traversing the invisible barrier typically distract a surgeon, and so such changes are undesirable. For this reason, statistics of the entire viewable scene are taken in one aspect. In this aspect, the statistics are generated for the entire captured frame, because the entire frame is used to generate the displayed scene. In another aspect, pixels that are not used in generating the displayed scene are not included in the statistics, e.g., the video processing crops the captured frame to obtain the displayed scene and so the cropped pixels are not used in generating the statistics.

Hence, in one aspect, statistics module 231 generates a brightness histogram for all the pixels locations in a frame captured by an image sensor of camera 220. At each pixel location in the frame, there are red, green, and blue pixels. Statistics module 231 converts the red, green, and blue pixel values to a value proportional to a brightness for that pixel location, e.g., an image luminance.

Figure 3:
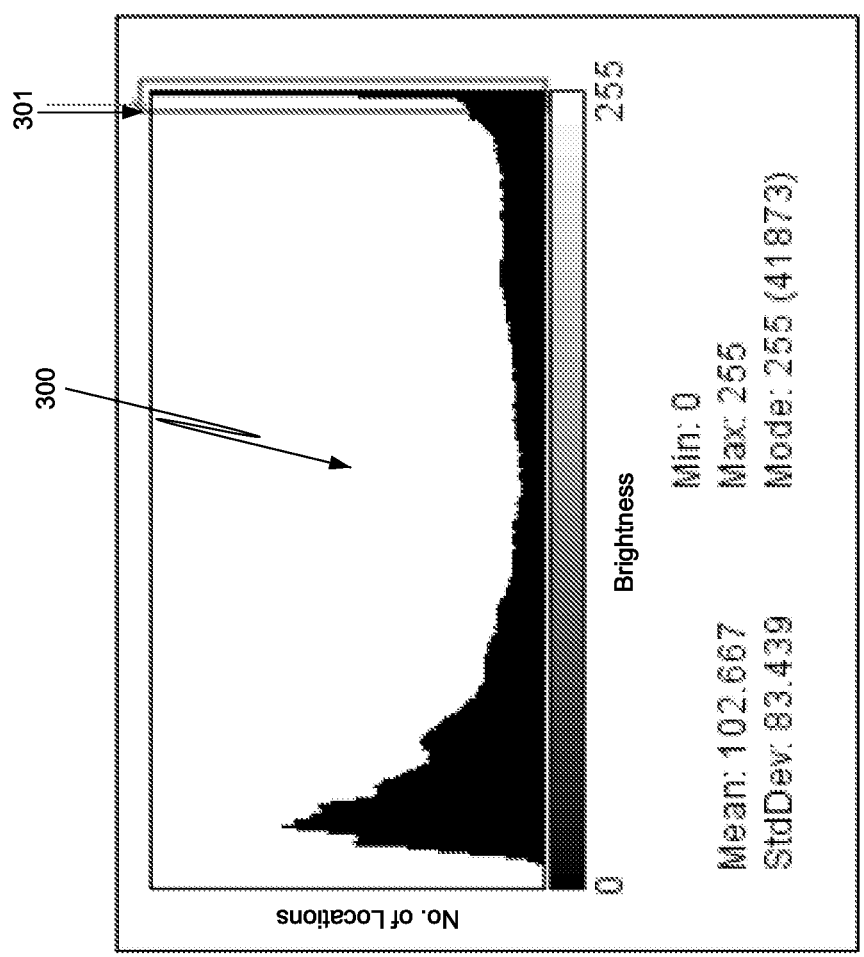
FIG. 3 is a brightness histogram of a captured scene that is generated by a statistics module.

Statistics module 231 counts the number of pixel locations in the frame having each of the possible brightness values and generates a histogram. If the brightness is represented by a one byte number there are two-hundred fifty-six possible brightness values ranging from zero to 255. FIG. 3 shows a typical histogram 300 of a frame that includes saturated pixels. The possible brightness values are plotted on an x-axis. A height of a bar for each of the brightness values represents the number of pixels locations in the frame having that brightness value. Also, along the x-axis is a gray-scale representation of the brightness.

Statistics module 231 generates the statistics for the captured frame without needing a frame buffer, and so not only does not require additional storage for the frame being processed, but also eliminates the time required to store and read from a frame buffer.

Figure 4:
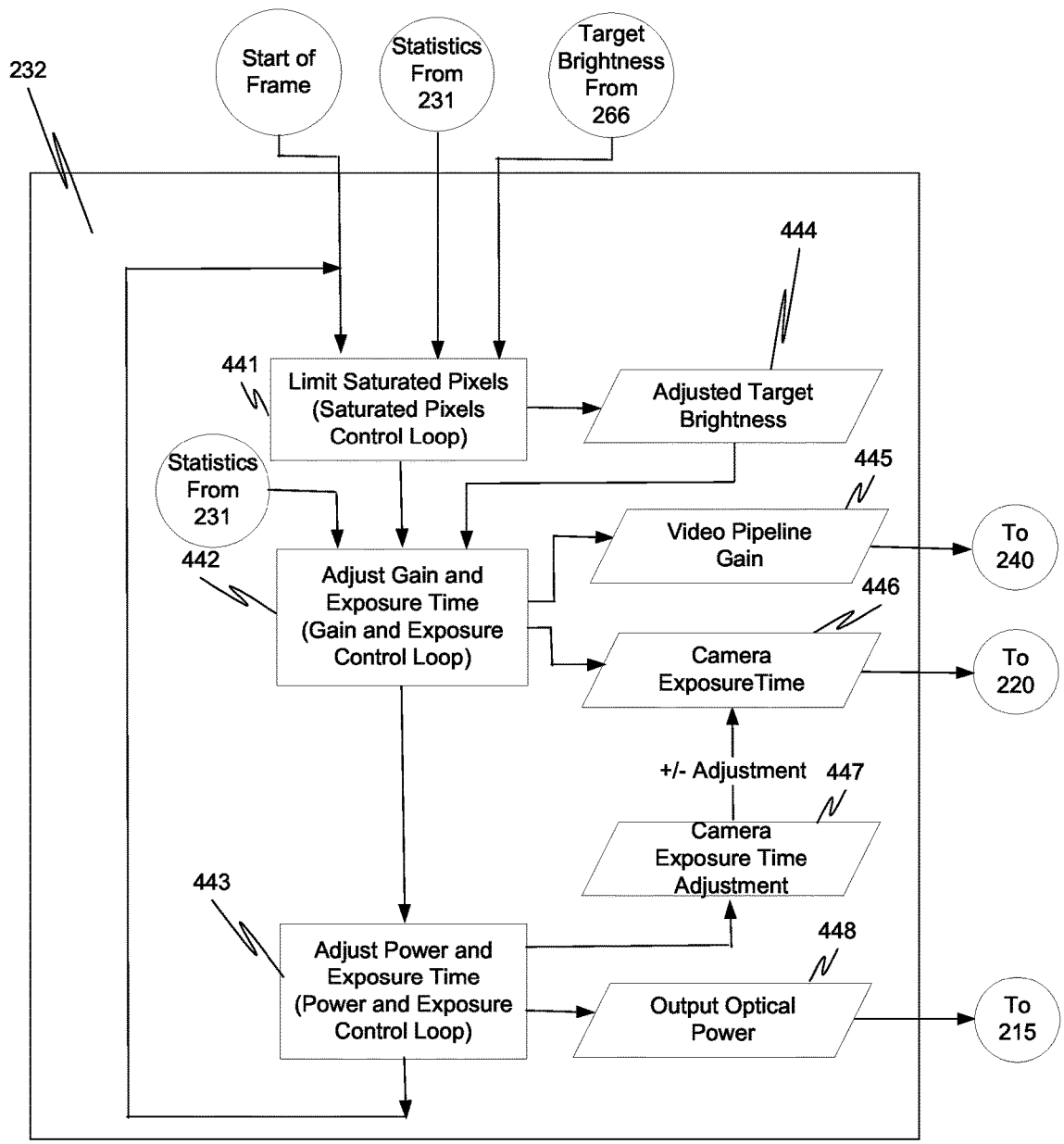
FIG. 4 is a process flow diagram for one aspect of an auto-exposure module.

FIG. 4 is a process flow diagram for one aspect of auto-exposure module 232. In this aspect, auto-exposure module 232 includes a LIMIT SATURATED PIXELS process 441, sometimes referred to as process 441, an ADJUST GAIN AND EXPOSURE TIME process 442, sometimes referred to as process 442, and an ADJUST POWER AND EXPOSURE TIME process 443, sometimes referred to as process 443.

Auto-exposure module 232 implements the three control loops of FIGS. 1A and 1B. A first control loop (saturate pixels control loop 133) includes LIMIT SATURATED PIXELS process 441, a second control loop (gain and exposure control loop 131) includes ADJUST GAIN AND EXPOSURE TIME process 442, and a third control loop (power and exposure control loop 132) includes ADJUST POWER AND EXPOSURE TIME process 443. Time constants are selected for these three control loops so that the control provided by auto-exposure module 232 is stable. The first control loop that includes LIMIT SATURATED PIXELS process 441 has a longer time constant relative to the time constant of second control loop that includes ADJUST GAIN AND EXPOSURE TIME process 442. The third control loop that includes ADJUST POWER AND EXPOSURE TIME process 443 has a longer time constant relative to the time constant of the second control loop. While FIG. 4 illustrates three processes 441, 442, and 443, in some aspects only processes 442 and 443 are implemented. See FIG. 1A.

Figure 5A:
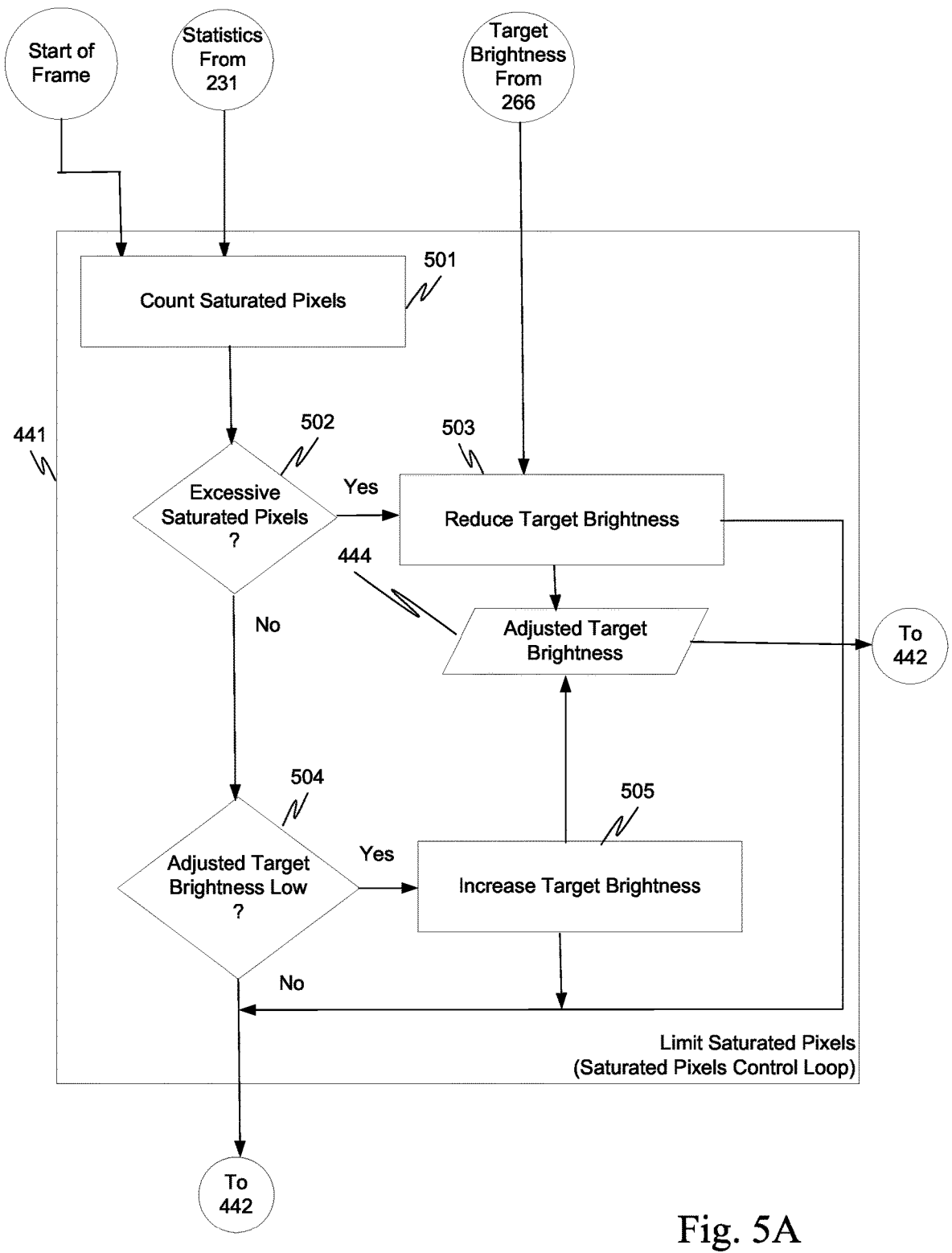
FIG. 5A is a process flow diagram for one of aspect of a limit saturated pixel process in FIG. 4.

As described more completely below, LIMIT SATURATED PIXELS process 441 minimizes over time the total screen area of display 251 that is consumed by saturated pixels. LIMIT SATURATED PIXELS process 441 controls ADJUSTED TARGET BRIGHTESS 444 to perform this minimization. FIG. 5A is a process flow diagram for one aspect of LIMIT SATURATED PIXELS process 441. Upon completion, LIMIT SATURATED PIXELS process 441 transfers to ADJUST GAIN AND EXPOSURE TIME process 442.

ADJUST GAIN AND EXPOSURE TIME process 442 controls the video pipeline gain and camera exposure time. ADJUST GAIN AND EXPOSURE TIME process 442 adjusts one of VIDEO PIPELINE GAIN 445 and CAMERA EXPOSURE TIME 446 based on the relationship of an average frame brightness to ADJUSTED TARGET BRIGHTNESS 444. VIDEO PIPELINE GAIN 445 provides video pipeline gain 236. CAMERA EXPOSURE TIME 446 provides camera exposure time 238.

Figure 5B:
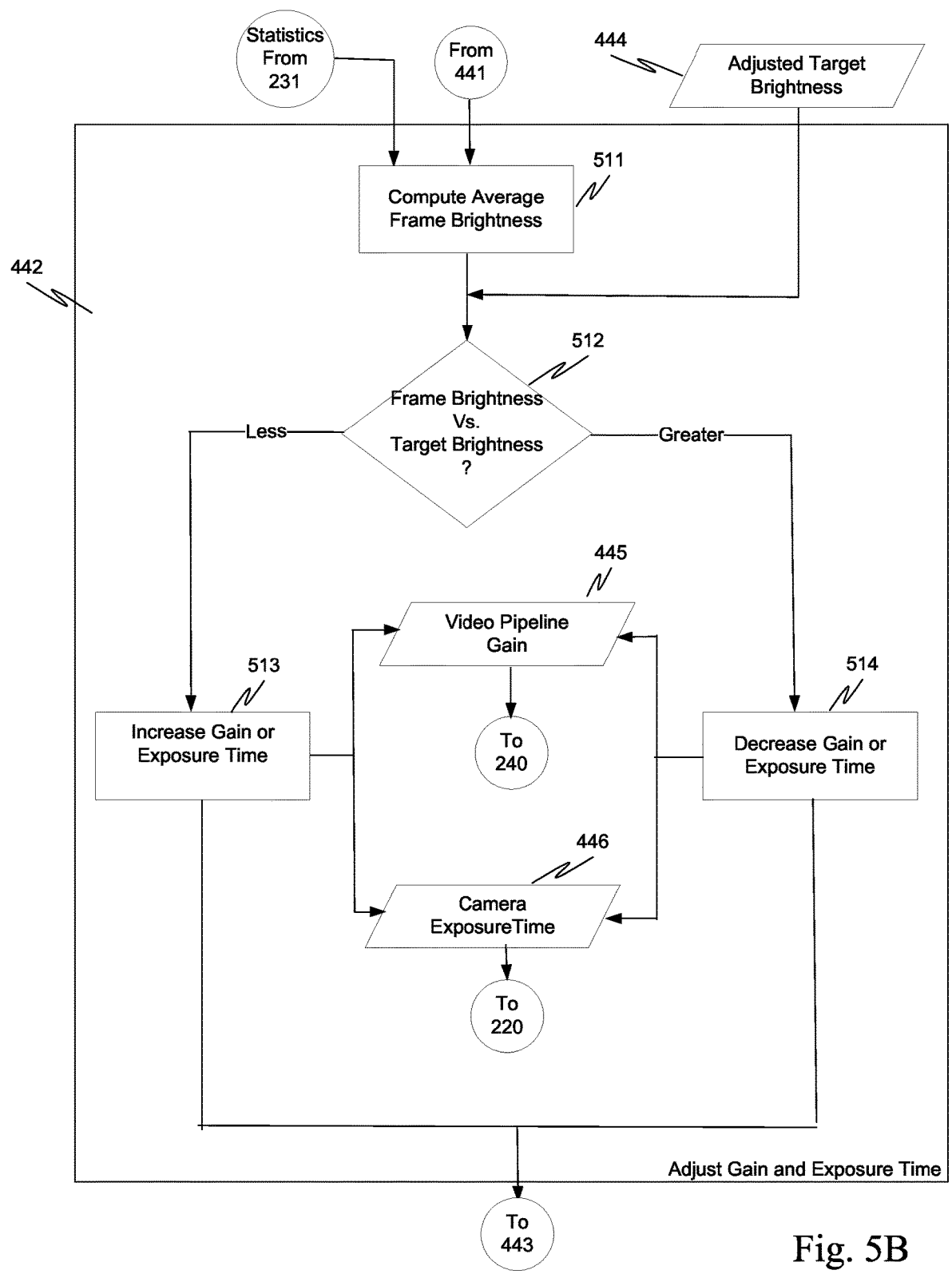
FIG. 5B is a process flow diagram for one aspect of an adjust gain and exposure time process in FIG. 4.

FIG. 5B is a process flow diagram for one aspect of ADJUST GAIN AND EXPOSURE TIME process 442. Upon completion, ADJUST GAIN AND EXPOSURE TIME process 442 transfers to ADJUST POWER AND EXPOSURE TIME process 443.

Figure 5C:
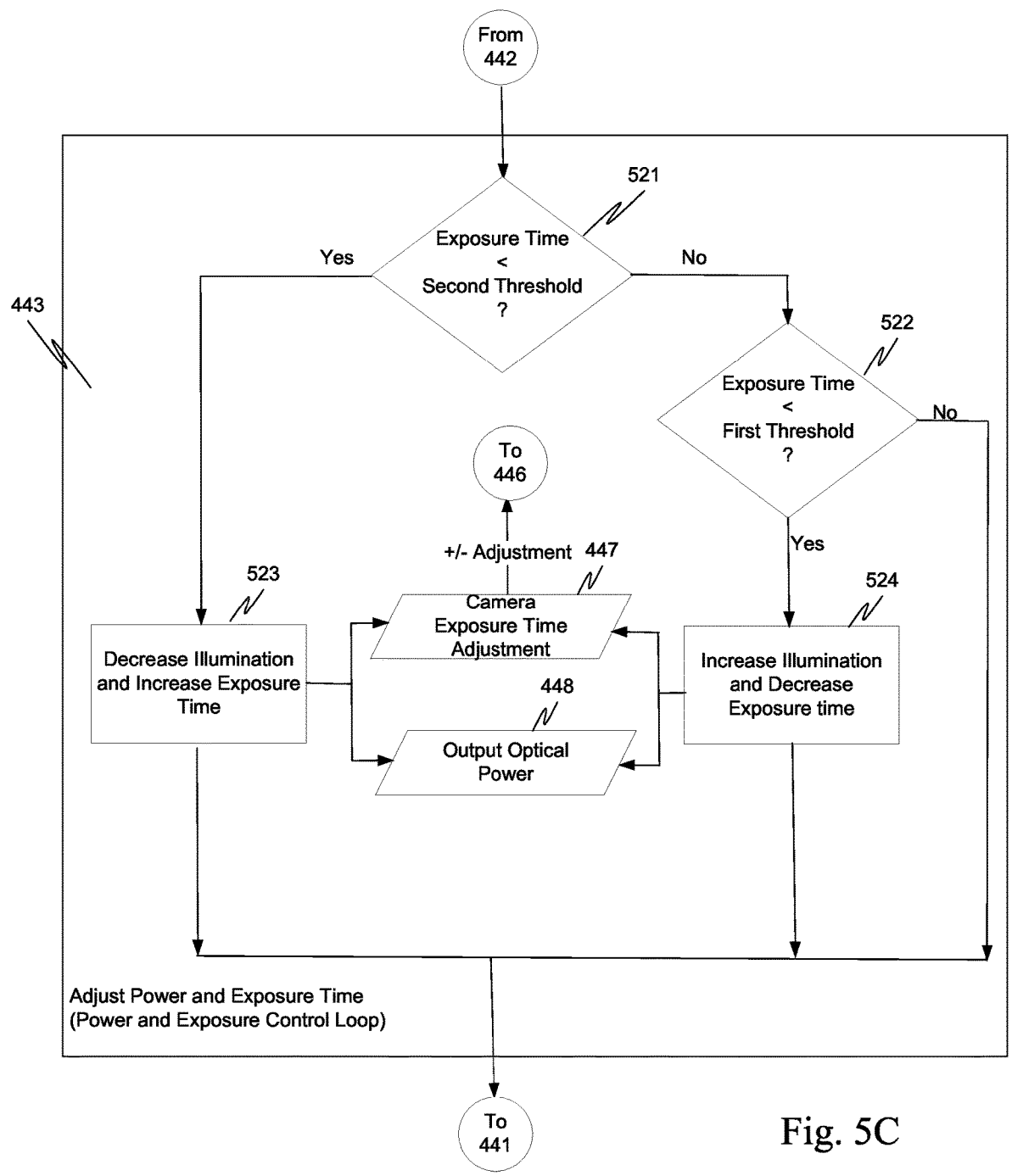
FIG. 5C is a process flow diagram for one aspect of an adjust power and exposure time in FIG. 4.

ADJUST POWER AND EXPOSURE TIME process 443 controls the output optical power of illuminator 210 and the camera exposure time. If the camera exposure time is less than a second exposure threshold (see FIG. 6), the output optical power is decreased and a positive adjustment is applied to camera exposure time to compensate for the illumination change. If the camera exposure time is greater than a first exposure threshold (see FIG. 6), the output optical power of illuminator 210 is increased and a negative adjustment is applied to camera exposure time to compensate for the illumination change. Thus, ADJUST POWER AND EXPOSURE TIME process 443 determines whether a change of OUTPUT OPTICAL POWER 448 and a CAMERA EXPOSURE TIME ADJUSTMENT 447 are needed, and then returns processing to LIMIT SATURATED PIXELS process 441 for processing of the next frame. OUTPUT OPTICAL POWER 448 provides output optical power 237. FIG. 5C is a process flow diagram for one aspect of ADJUST POWER AND EXPOSURE TIME process 443.

As indicated above, FIG. 5A illustrates one aspect of LIMIT SATURATED PIXELS process 441. COUNT STATURATED PIXELS process 501 counts the he number of pixels in the highest bin(s) of histogram 300. If the number of pixels in the highest bin(s), e.g., bin 255, is larger than a saturated pixel threshold, EXCESSIVE STATURATED PIXELS check process 502 transfers to REDUCE TARGET BRIGHTNESS process 503 and otherwise transfers to ADJUSTED TARGET BRIGHTNESS LOW check process 504. While COUNT STATURATED PIXELS process 501 is shown in this aspect as being included in LIMIT SATURATED PIXELS process 441, COUNT STATURATED PIXELS process 501 could be included in statistics module 231 instead of LIMIT SATURATED PIXELS process 441.

In one aspect, COUNT STATURATED PIXELS process 501, sometimes referred to as process 501, counts the number of saturated pixels 301 in histogram 300. In the example of FIG. 3, the count of saturated pixels in bin 255 is 41873.

If endoscope 201 is a stereoscopic endoscope, statistics module 231 generates a histogram for each of the left and right optical channels. If endoscope 201 is not a stereoscopic endoscope, statistics module 231 generates a histogram for the single optical channel. In one aspect, two bytes are used to represent the brightness and so the histograms have 512 bins along the x-axis. COUNT STATURATED PIXELS process 501 determines the number of saturated pixels, in one aspect, as the sum of the number of pixels in bin 511 of each of the left and right histograms.

Some modes of operation of teleoperated surgical system 200 can mark one of the left scene and the right scene as invalid. In these modes of operation, the count of saturated pixels is done for the histogram of the valid scene.

In one aspect, the saturated pixel threshold for the number of saturated pixels allowed in a scene was empirically determined. A teleoperated surgical system 200 was configured to vary the size of a saturated region in a scene displayed on display unit 251. Clinical trials with such a system were used to determine the threshold for the number saturated pixels and the bins used to count the number of saturated pixels so that a set of surgical tasks could be performed without users of the system labeling saturated regions as distracting or hindering accomplishment of the task.

In one aspect, with five hundred twelve bins in the histogram (labelled bin 0 to bin 511) and a stereoscopic endoscope, the saturated pixel threshold was selected as 12000 in bin five hundred eleven. Thus, for this aspect, EXCESSIVE STATURATED PIXELS check process 502 compared the saturated pixel threshold of 120000 with the sum of the total number of saturated pixels in bin 511 of the left histogram and the total number of saturated pixel in bin 511 of the right histogram received from statistics module 231. By adjusting the maximum saturated pixel count, and the number of bins used to count saturated pixels, auto-exposure module 232 can be tuned for size of the saturated region on the screen, and can compensate for gains later in the video pipeline. If the number of saturated pixels in a frame is greater than the saturated pixel threshold, check process 502 transfers to REDUCE TARGET BRIGHTNESS process 503.

Using the total number of saturated pixels in the same bin of left and right frames gives a measure of the total area of saturated pixels in the displayed scene, and is independent of the position of the saturated pixels on the screen (i.e., a saturated pixel region can move throughout the field-of-view of the camera with little change to the histogram of pixels). Nevertheless, when the number of saturated pixels exceeds the saturated pixel threshold, the target brightness is lowered by REDUCE TARGET BRIGHTNESS process 503. Consequently, large regions of saturated pixels can cause auto-exposure module 232 to dim the displayed scene such that the non-reflective areas of the scene are too dark. For this reason, the reduction in target brightness is range-limited.

In one aspect, the time constant for LIMIT SATURATED PIXELS process 441 is four to five seconds, and the maximum reduction in target brightness, the range limit on target brightness, is thirty-five percent of the original target brightness 266. The range limit on target brightness is empirically determined. The range is determined ascertaining the lowest average brightness of displayed scenes that users identify as providing information that can be used in the surgical produce. The ratio of the lowest average brightness to the original target brightness is used to define the range limit on target brightness, e.g., Target Brightness Range Limit=(1−(lowest acceptable average brightness/original target brightness))*100

To determine the allowed change of target brightness per frame, for a five-second time constant and a thirty-five percent brightness range limit, a change of seven percent per second is permitted. For a camera that captures sixty frames per second, the change in target brightness per frame is a fixed linear step of 0.11 percent until either the number of saturated pixels in a captured scene is smaller than the saturated pixel threshold, or the change from initial target brightness 266 is range limited, e.g., the target brightness is reduced by the target brightness range limit. In this example, for an initial target brightness of 1500 and a range limit of thirty-five percent, the limit on target brightness is (1500* (1-0.35)), which is a limit of 975.

Thus, if the adjusted target brightness is not at the limit of the target brightness range, REDUCE TARGET BRIGHTNESS process 503 changes the adjusted target brightness by one fixed size linear step and saves the result as ADJUSTED TARGET BRIGHTNESS 444. After adjusting the target brightness, LIMIT SATURATED PIXELS process 441 transfers to ADJUST GAIN AND EXPOSURE TIME process 442. If the adjusted target brightness is at the limit of the target brightness range, i.e., the target brightness is range limited, REDUCE TARGET BRIGHTNESS process 503 takes no action and transfers to process 442.

If the number of pixels in the highest bin(s) is smaller than the saturated pixel threshold, EXCESSIVE STATURATED PIXELS check process 502 transfers to ADJUSTED TARGET BRIGHTNESS LOW check process 504, sometimes referred to as process 504. Process 504 compares ADJUSTED TARGET BRIGHTNESS 444 to original target brightness 266. If ADJUSTED TARGET BRIGHTNESS 444 is smaller than original target brightness 266, process 504 transfers to INCREASE TARGET BRIGHTNESS process 505, and otherwise to transfers to ADJUST GAIN AND EXPOSURE TIME process 442.

INCREASE TARGET BRIGHTNESS process 505 increases the adjusted exposure time by one fixed linear step of the size described above, and saves the result as ADJUSTED TARGET BRIGHTNESS 444. Process 505 transfers to ADJUST GAIN AND EXPOSURE TIME process 442.

As indicated above, FIG. 5B illustrates one aspect of ADJUST GAIN AND EXPOSURE TIME process 442. COMPUTE AVERAGE FRAME BRIGHTNESS process 511, sometimes referred to as process 511, determines a mean of the brightness, sometimes referred to as average brightness, from the brightness histogram. As noted above, if endoscope 201 is a stereoscopic endoscope, statistics module 231 generates a histogram for each of the left and right optical channels. If endoscope 201 is not a stereoscopic endoscope, statistics module 231 generates a single histogram. Thus, for a stereoscopic endoscope, process 511 determines a left mean brightness for the left scene captured from the left optical channel, and determines a right mean brightness for the right scene captured from the right optical channel. The left mean brightness and the right mean brightness are averaged by process 501 to obtain the average frame brightness—the overall brightness of the frame. While COMPUTE AVERAGE FRAME BRIGHTNESS process 511 is shown in this aspect as being included in ADJUST GAIN AND EXPOSURE TIME process 442, COMPUTE AVERAGE FRAME BRIGHTNESS process 511 could be included in statistics module 231 instead of ADJUST GAIN AND EXPOSURE TIME process 442.

Some modes of operation of teleoperated surgical system 200 can mark one of the left scene and the right scene as invalid. In these modes of operation, the mean of the valid scene is taken as the average frame brightness by process 511. After determining the average frame brightness, process 511 transfers processing to FRAME BRIGHTNESS VS. TARGET BRIGHTNESS check process 512.

FRAME BRIGHTNESS VS. TARGET BRIGHTNESS check process 512, sometimes referred to as check process 512, compares the average frame brightness with ADJUSTED TARGET BRIGHTNESS 444. If the average frame brightness is greater than ADJUSTED TARGET BRIGHTNESS 444, check process 512 transfers to DECREASE GAIN OR EXPOSURE TIME process 514. If the average frame brightness is less than ADJUSTED TARGET BRIGHTNESS 444, check process 512 transfers to INCREASE GAIN OR EXPOSURE TIME process 513.

When processing transfers to INCREASE GAIN OR EXPOSURE TIME process 513, sometimes referred to process 513, the brightness of the captured image is too low. If the camera exposure time is not at a maximum camera exposure time Emax (see FIG. 6), process 513 increases the camera exposure time, which in turn increases the average frame brightness of subsequently captured frames. However, if the camera exposure time is at maximum camera exposure time Emax, the camera exposure time cannot be increased further. In this situation, process 513 increases the video pipeline gain.

Thus, process 513 first determines the ratio of ADJUSTED TARGET BRIGHTNESS 444 to the average frame brightness. Since the average frame brightness is less than ADJUSTED TARGET BRIGHTNESS 444, the ratio is greater than one. As an example, assume the ratio is 1.2, e.g., the brightness needs to be increased by twenty percent. Brightness is a linear function of camera exposure time. Thus, if CAMERA EXPOSURE TIME 446 is less than maximum camera exposure time Emax, process 513 multiplies CAMERA EXPOSURE TIME 446 by the ratio of ADJUSTED TARGET BRIGHTNESS 444 to the average frame brightness, e.g., the camera exposure time is multiplied by 1.2, and the result is saved as CAMERA EXPOSURE TIME 446. If CAMERA EXPOSURE TIME 446 is at maximum camera exposure time Emax, process 513 multiplies VIDEO PIPELINE GAIN 445 by the ratio of ADJUSTED TARGET BRIGHTNESS 444 to the average frame brightness, e.g., the video pipeline gain is multiplied by 1.2, and the result is saved as VIDEO PIPELINE GAIN 445. If multiplying CAMERA EXPOSURE TIME 446 by the ratio of ADJUSTED TARGET BRIGHTNESS 444 to the average frame brightness gives a camera exposure time that is greater than maximum camera exposure time Emax, the increase is split between the camera exposure time and the video pipeline gain so that CAMERA EXPOSURE TIME 446 is at camera exposure time Emax and the remainder of the increase is applied to VIDEO PIPELINE GAIN 445. For the example with the twenty percent increase, if CAMERA EXPOSURE TIME 446 is ten percent less than maximum camera exposure time Emax, CAMERA EXPOSURE TIME 446 is increased so that CAMERA EXPOSURE TIME 446 is at maximum camera exposure time Emax and VIDEO PIPELINE GAIN 445 is increased by the remainder, e.g.,

NEW VIDEO PIPELINE GAIN=1.2*(1.0−0.1)=1.08

Upon completion, process 513 transfers to ADJUST POWER AND EXPOSURE TIME process 443.

When processing transfers to DECREASE GAIN OR EXPOSURE TIME process 514, sometimes referred to process 514, the brightness of the captured image is too high. If the video pipeline gain is greater than one (see FIG. 6), process 514 decreases the video pipeline gain, which decreases the brightness of the displayed scenes. However, if video pipeline gain equals one, process 514 decreases the camera exposure time, which reduces the average frame brightness of subsequently captured images.

Thus, process 514 first determines the ratio of ADJUSTED TARGET BRIGHTNESS 444 to the average frame brightness. Since the average frame brightness is greater than ADJUSTED TARGET BRIGHTNESS 444, the ratio is less than one. As an example, assume the ratio is 0.8, e.g., the brightness needs to be decreased by twenty percent.

If VIDEO PIPELINE GAIN 445 is greater than one, process 514 multiplies VIDEO PIPELINE GAIN 445 by the ratio of ADJUSTED TARGET BRIGHTNESS 444 to the average frame brightness, e.g., the video pipeline gain is multiplied by 0.8, and the result is saved as VIDEO PIPELINE GAIN 445. If VIDEO PIPELINE GAIN 445 is one, process 514 multiplies CAMERA EXPOSURE TIME 446 by the ratio of ADJUSTED TARGET BRIGHTNESS 444 to the average frame brightness, e.g., the camera exposure time is multiplied by 0.8, and the result is saved as CAMERA EXPOSURE TIME 446. If multiplying VIDEO PIPELINE GAIN 445 by the ratio of ADJUSTED TARGET BRIGHTNESS 444 to the average frame brightness gives a video pipeline gain of less than one, the decrease is split between the camera exposure time and the video pipeline gain so that VIDEO PIPELINE GAIN 445 is at one and the remainder of the decrease is applied to CAMERA EXPOSURE TIME 446. For the example with the twenty percent decrease, if VIDEO PIPELINE GAIN 445 is 1.1, VIDEO PIPELINE GAIN 445 is decreased to one, and CAMERA EXPOSURE TIME 446 is decreased the remainder of the decrease, e.g.,

NEW CAMERA EXPOSURE TIME=CAMERA EXPOSURE TIME*(1−0.2)/(1/1.1))

Upon completion, process 514 transfers to ADJUST POWER AND EXPOSURE TIME process 443.

ADJUST POWER AND EXPOSURE TIME process 443 controls output optical power of illuminator 210 by sending a command to illumination controller 215 with the desired output optical power of light source 211 and a sends a corresponding exposure time adjustment to CAMERA EXPOSURE TIME 446. The change in output optical power and camera exposure time is synchronized as explained below with respect to FIG. 7.

FIG. 5C is a process flow diagram for one aspect of ADJUST POWER AND EXPOSURE TIME process 443. However, prior to considering FIG. 5C, parameters used in the processes of FIG. 5C are considered.

In one aspect, process 443 increases or decreases the brightness of the illumination output from light source 211 in fixed-size, synchronized steps. The camera exposure time is changed the same percentage as the change in illumination, e.g., if a step change multiplies the illumination output by 1.006, the camera exposure time is divided by 1.006.

To ascertain the fixed size of a step, a ramp time tramp, in seconds, is specified as the time period used to linearly ramp the illumination output from light source 211 from a minimum output optical power Pmin to a maximum output optical power Pmax, and conversely.

The fixed size output optical power step Pstep is defined as:

$P\text{step}=(P\text{max}-P\text{min})/(\text{tramp}*(\text{Frames/sec of camera}))$.

As an example, consider a maximum output optical power of 800 milliwatts, a minimum output optical power of 400 milliwatts, a ramp time tramp of three seconds, and a camera that captures sixty frames per second. The fixed size step is ±2.22 milliwatts/frame, if the output optical power is changed. If the current output optical power is 400 mW, the illumination output is multiplied by (1+ (2.22/400)) or 1.0056. Thus, the camera exposure time is divided by 1.0056.

As indicated above, a change in illumination should not produce a noticeable flicker in the displayed scene. Hence, the ramp time is selected so that the change in illumination does not produce noticeable brightness flicker in the scene displayed on display unit 251, and so that the three control loops are stable, e.g., the ramp time is the time constant for the third control loop. Thus, in these examples, the time constant for the first control loop is five seconds, and the time constant for the third control loop is three seconds.

The new output optical power Pnew at the distal tip of endoscope 201 is the current output optical power Pcurrent plus or minus the output optical power step Pstep, i.e., $$Pnew=Pcurrent+Pstep$$

where, for this example, output optical power step Pstep is one of zero, +2.22, or −2.22. Which of the three possible values for output optical power step Pstep is used depends on the value of the camera exposure time, as described below. Also, as explained more completely below with respect to FIG. 7, the change in output optical power and exposure time is synchronized to a pipeline frame time.

While the step change in output optical power per frame is known, illumination controller 215 controls current to each light source of plurality of light sources 211, when the light sources are LEDs. However, the output optical power of an LED is not linear with respect to a change in current. Thus, a look-up table is used to convert the commanded change in output optical power to a current for each of the LEDs so that the output optical power is provided at the distal tip of endoscope 201.

The values in the look-up table are determined by calibration of the light source 211 to a known standard. The output optical power is at the distal tip of endoscope 201, and so the current for each LED is determined so that the actual output of light source 211 is enough higher to account for any attenuation of the light between the output of light source 211 and the distal tip of endoscope 201.

In one aspect, maximum output optical power Pmax is selected so that at a minimum working distance between the distal tip of endoscope 201 and target 203, maximum output optical power Pmax does not produce tissue damage.

The minimum output optical power Pmin is selected to that at a minimum working distance between the distal tip of endoscope 201 and target 203, the noise in the displayed scene is below a threshold, and the output optical power is above the minimum achievable output optical power of illuminator 210.

To ascertain whether the change in illumination output increases, decreases, or stays the same, the value of the camera exposure time is used. At very small camera exposure times in Region Three 603 (FIG. 6) where the average captured scene brightness is high, the output optical power is dimmed. Specifically, for each consecutive frame that has a camera exposure time in Region Three 603, the output optical power is decreased by output optical power Pstep and the exposure time of camera 220 is increased by the same percentage as the percentage decease in the output optical power. If output optical power step Pstep would decrease the illumination output below minimum output optical power Pmin, the illumination output is not changed and the illumination output is maintained at minimum output optical power Pmin and the exposure time of camera 220 is not changed.

Assuming that the increase in exposure time and corresponding decrease in illumination results in a captured image with about the same average brightness as previously captured images, the camera exposure time increases towards Region Two 602.

At very high camera exposure times in Region One 601, where captured average scene brightness, overall scene brightness, is low, the output optical power is increased. Specifically, for each consecutive frame that has an exposure time in Region One 601, the output optical power is increased by output optical power step Pstep and the exposure time of camera 220 is decreased by the same percentage as the percentage increase in the output optical power. If the change in output optical power would increase the illumination output above maximum output optical power Pmax, the illumination output is not changed and the illumination output is maintained at maximum output optical power Pmax and the exposure time of camera 220 is not changed.

Assuming that the decrease in exposure time and corresponding increase in illumination results in a captured image with about the same average brightness as previously captured images, the camera exposure time decreases towards Region Two 602.

Thus, the control loop including ADJUST POWER AND EXPOSURE TIME process 443 changes the illumination so that the illumination output goes towards the illumination output range as represented by Region Two 602. Region Two 602 is a hysteresis region.

To the extent possible, the desire is to minimize illumination changes. Even though a change in brightness associated with an illumination change might not be noticeable to a surgeon over a portion of the scene that is located at an average working distance between the distal tip of endoscope 201 and target 203, at locations in the scene that are at greater than the average working distances, surgeons tend to notice changes in brightness which can be distracting. Thus, Region Two 602, in which no illumination or exposure changes are made with a change in camera exposure time, is allocated fifty percent of the range of possible camera exposure times in this aspect. In view of this disclosure, the range of Region Two 602 can be selected as other than fifty percent of the range of possible camera exposure times.

Thus, as shown in FIG. 6, if ADJUST POWER AND EXPOSURE TIME process 443 configures the output optical power and the camera exposure time based upon a value of a camera exposure time. The third control loop, power and exposure control loop 132, increases the illumination output and decreases camera exposure time if the camera exposure time is larger than a first exposure threshold so long as the output optical power is less than a maximum output optical power Pmax. The third control loop decreases the output optical power and increases the camera exposure time when the camera exposure time is smaller than a second exposure threshold so long as the output optical power is greater than a minimum output optical power Pmin. The third control loop leaves the output optical power and the camera exposure time unchanged if the exposure time is between the first exposure threshold and the second exposure threshold.

In one aspect the maximum output optical power Pmax corresponds to an output optical power 800 milliwatts. The minimum output optical power Pmin corresponds to an output optical power of 400 milliwatts, the maximum camera exposure time Emax is 4096, and the minimum camera exposure time Emin is zero.

Going to FIG. 5C, EXPOSURE TIME LESS THAN SECOND THRESHOLD check process 521, sometimes referred to as process 521 determines whether CAMERA EXPOSURE TIME 446 is less than the second exposure threshold. If CAMERA EXPOSURE TIME 446 is less than the second exposure threshold, process 521 transfers processing to DECREASE ILLUMINATION AND INCREASE EXPOSURE TIME process 523, and otherwise transfers processing to EXPOSURE TIME LESS THAN FIRST THRESHOLD check process 522.

When processing transfers to DECREASE ILLUMINATION AND INCREASE EXPOSURE TIME process 523, sometimes referred to as process 523, CAMERA EXPOSURE TIME 446 is in Region Three 603. Thus, so long as the illumination output is greater than a minimum output optical power Pmin, process 523 decreases OUTPUT OPTICAL POWER 448, e.g., output optical power Pcurrent, by output optical power step Pstep. Process 523 also loads a step increase into CAMERA EXPOSURE TIME ADJUSTMENT 447, which, in turn, increases CAMERA EXPOSURE TIME 446. If the illumination output equals minimum output optical power Pmin, process 523 takes no action. DECREASE ILLUMINATION AND INCREASE EXPOSURE TIME process 523 transfers processing to LIMIT SATURATED PIXELS process 441.

If check process 521 transfers processing to EXPOSURE TIME LESS THAN FIRST THRESHOLD check process 522, check process 522 determines whether CAMERA EXPOSURE TIME 446 is less than the first exposure threshold. If CAMERA EXPOSURE TIME 446 is less than the first exposure threshold, check process 522 transfers processing INCREASE ILLUMINATION AND DECREASE EXPOSURE TIME process 524, and otherwise transfers processing to LIMIT SATURATED PIXELS process 441.

When processing transfers to INCREASE ILLUMINATION AND DECREASE EXPOSURE TIME process 524, sometimes referred to as process 524, CAMERA EXPOSURE TIME 446 is in Region One 601. Thus, so long as the illumination output is less than maximum output optical power Pmax, process 524 increases OUTPUT OPTICAL POWER 448, e.g., output optical power Pcurrent, by output optical power step Pstep. Process 524 also loads a step decrease into CAMERA EXPOSURE TIME ADJUSTMENT 447, which, in turn, decreases CAMERA EXPOSURE TIME 446. If the output optical power equals maximum output optical power Pmax, process 524 takes no action. INCREASE ILLUMINATION AND DECREASE EXPOSURE TIME process 524 transfers processing to LIMIT SATURATED PIXELS process 441.

When ADJUST POWER AND EXPOSURE TIME process 443 is completed, processing returns to LIMIT SATURATED PIXELS process 441. Thus, processes 441 to 443 are repeated for each captured frame.

To make illumination changes invisible to the user of teleoperated surgical system 200, the illumination change is synchronized with the compensating change in camera exposure time, such that the overall brightness of the video displayed to the surgeon remains about constant with a change in illumination. For example, a decrease in output optical power and an increase in camera exposure time must occur on the same video frame. Here, about constant means constant to within tolerances of teleoperated surgical system 200.

The processing of the video stream in teleoperated surgical system 200 has delays. Illumination control, video pipeline gain control, camera exposure control, video statistics collection and analysis are all at different pipeline delays. For example, at frame time t0, (FIG. 7) for a first frame 701 of the video stream, a frame is captured statistics are gathered for frame 701 by statistics module 231 and a gain from a previously captured frame is written to the video pipeline.

At frame time t1, an illumination output, and a camera exposure time are calculated by auto-exposure module 232 and the camera exposure time is written to camera 220. At the start of frame time t2, the output optical power is changed to new output optical power Pnew. Then, a frame 702 is captured by the camera at frame time t3 with the exposure time and output optical power generated using first frame 701. Thus, the new exposure time and output optical power are synchronized for the capture of frame 702.

These steps are pipelined so that an exposure time and illuminator brightness are applied for every frame of video. In one aspect, pipeline synchronization is achieved by attaching metadata to the video frame synchronization signals that travel throughout system 200 with the video stream, i.e., attaching metadata to each frame in the video stream. The metadata includes camera exposure time, illuminator brightness, and video pipeline gain.

In one aspect, teleoperated surgical system includes a method of increasing illumination in the surgical field via surgeon command, and a method for detecting contact between tissue and endoscope 201. When tissue contact is detected, the illumination from endoscope 201 is automatically reduced to levels safe for tissue contact.

The signal-to-noise ratio of a scene displayed on display unit 251 decreases with decreased light reflected back from illuminated target 203 to the image sensor of camera 220. This decrease in signal-to-noise ratio can limit the usable working distance 204 (the distance between the endoscope tip and imaging target 203) of endoscope 201.

However, there is a trade-off between output optical power level and risk of tissue damage. As stated, increased output optical power can result in an increase in usable working distance 204. However, increased output optical power can also result in an increased risk of tissue damage if the output optical power is high enough, and the working distance is low enough, such that the incident light exceeds non-damaging levels. An increased risk of tissue damage can occur either due to increased optical power density of the incident light, or due to increased temperature of the endoscope tip contacting tissue. In either case, lower output optical power levels result in less risk.

To avoid the risk of tissue damage, the output optical power levels from endoscope 201 are limited such that the output optical power levels are safe for direct contact between the endoscope tip and tissue. This, however, limits the maximum working distance of endoscope 201. For purpose of example, consider that output optical power levels less than one watt are typically considered safe. However, in one aspect, teleoperated surgical system 200 includes a high beam mode of operation in which the output optical power is larger than a safe output optical power, e.g., an output optical power of more than one watt such as 1.5 watts.

In one aspect, the high beam mode of operation, sometimes referred to as high power mode of operation, is initiated by a surgeon activating a physical switch 265 on the surgeon's console. In another aspect, the high beam mode of operation is initiated by the surgeon clicking on a switch presented in a user interface that is displayed on display unit 251.

With the surgeon in control of the high-beam mode, the high beam mode of operation should only be activated when there is a low risk of tissue damage, because in this mode of operation the output optical power is larger than what is considered safe. Surveying the surgical field in abdominal procedures would be a typical application for the high-beam mode of operation. However, there is still a risk of the surgeon inadvertently moving endoscope 201 too close to tissue, or a risk of unintentional contact with tissue.

If endoscope 201 is inadvertently moved too close to tissue, the average brightness of the captured images increases, and so auto-exposure module 232 reduces the camera exposure time, as explained above. As the camera exposure time continues to decrease, the exposure time reaches Region Three 603. Then, auto-exposure module 232 starts reducing the output optical power. Thus, the illumination increase caused by the inadvertent movement of endoscope 201 too close to tissue is automatically handled by auto-exposure module 232 by reducing the output optical power.

If endoscope 201 contacts tissue, the contact is detected by contact detection module 233, and the illumination is decreased to appropriate levels in either the normal mode of operation or in the high-beam mode of operation. Contact detection module 233 determines tissue contact by detecting when a change in output optical power—an increase or a decrease—does not result in a corresponding change in average reflected luminance from target 203, where the average reflected luminance is taken as the average brightness of a capture scene divided by the camera exposure time. The average brightness of a scene is determined by COMPUTE AVERAGE FRAME BRIGHTNESS process 511 (FIG. 5C) and the camera exposure time is available in CAMERA EXPOSURE TIME 446. Alternatively, COMPUTE AVERAGE FRAME BRIGHTNESS process 511 (FIG. 5C) could be incorporated in contact detection module 233 or statistics module 231.

For example, when the tip of the endoscope is covered, i.e., in contact with tissue, such that no light enters the camera lens, auto-exposure module 232 will increase the output optical power. However, the tissue contact still prevents the reflected light from reaching the camera. Consequently, there is no change in average reflected luminance when the output optical power is increased. Thus, contact detection module 233 detects tissue contact, and attenuates the output optical power to a level that is safe for tissue contact. In one aspect, safe output optical power for tissue contact is greater than minimum output optical power. However, if tissue damage is dominated by conductive heat from contact between endoscope tip and tissue, safe output optical power for tissue contact could be below the minimum output optical power.

In one aspect, contact detection module 233 disables the output optical power control of auto-exposure module 232 and commands illumination controller 215 to reduce the output optical power to a safe level. Alternatively, contact detection module 233 could command illumination controller 215 to active an attenuator in light source 211 that reduces the output optical power from light source 211 to the safe level.

In one aspect, the tissue contact detection is implemented as:

$$dL/dI=0$$

where
- dL is the change in average reflected luminance of two captured frames,
- dI is the change in output optical power for the two captured frame.

In another aspect, contact is detected when:

$$-\text{threshold} < dL/dI < \text{threshold}$$

where
- threshold encompasses measurement uncertainty and noise in the measurement of dL and dI.

Thus, a contact detection method utilizes varying output optical power. In a system with dynamic illumination control, the output optical power is varying as tissue approaches the tip of the endoscope. The auto-exposure control decreases the output optical power as the tissue approaches the tip of endoscope 201. Once the tissue contacts the tip of the endoscope 201, little or no change in reflected luminance is detected with a change in optical power. Upon detection of this condition, the illuminator brightness is attenuated, i.e., reduced, to a predetermined level that is safe for tissue contact, e.g., illumination Pmin.

In another aspect, instead of monitoring the change in reflected luminance with the change in output optical power, a characteristic overall reflected luminance profile as tissue contacts the endoscope tip is used for contact detection, or improved contact detection. The characteristic overall reflected luminance profile can be either in the time domain or in the frequency domain. If the average reflected luminances determined from captured scenes matches the characteristic overall luminance profile to within a threshold amount, contact is detected. In one aspect, the characteristic overall reflected luminance profile is empirically determined by measuring the overall reflected luminance of scenes as the endoscope tip approaches and contacts tissues.

There may be conditions in which system 200 is stuck in the low brightness state if removal of the contacting tissue does not result in a reflected luminance change. To avoid "stuck" states, where output optical power of illuminator 210 is not varying, a low-rate output optical power dithering technique is employed. When tissue-contact is detected, contact detection module 233 enables a dither module 217. Dither module 217 varies the output optical power in a known manner about the safe level to increase reliability of detecting a non-contact state.

For example, dither module 217 may vary the output optical power from light source 211 in a known time varying manner, e.g., in a sinusoidal manner, about the safe level. If the time varying reflected low level output power reaches the camera, auto-exposure module 232 detects the changes in output optical power, e.g., detects changes in the average brightness of captured scenes, which means that the tip of endoscope 201 is no longer in contact with tissue. Thus, contact detection module 233 is reset so that auto-exposure module 232 can take control of the output optical power.

The various modules described herein can be implemented by software executing on a processor, hardware, firmware, or any combination of the three. When the modules are implemented as software executing on a processor, the software is stored in a memory as computer readable instructions and the computer readable instructions are executed on the processor. All or part of the memory can be in a different physical location than a processor so long as the processor can be coupled to the memory. Memory refers to a volatile memory, a non-volatile memory, or any combination of the two.

Also, the functions of the various modules, as described herein, may be performed by one unit, or divided up among different components, each of which may be implemented in turn by any combination of hardware, software that is executed on a processor, and firmware. When divided up among different components, the components may be centralized in one location or distributed across system 200 for distributed processing purposes. The execution of the various modules results in methods that perform the processes described above for the various modules.

A processor is coupled to a memory containing instructions executed by the processor. This could be accomplished within a computer system, or alternatively via a connection to another computer via modems and analog lines, or digital interfaces and a digital carrier line.

Herein, a computer program product comprises a computer readable medium configured to store computer readable code needed for any part of or all of the processes described herein, or in which computer readable code for any part of or all of those processes is stored. Some examples of computer program products are CD-ROM discs, DVD discs, flash memory, ROM cards, floppy discs, magnetic tapes, computer hard drives, servers on a network and signals transmitted over a network representing computer readable program code. A non-transitory tangible computer program product comprises a tangible computer readable medium configured to store computer readable instructions for any part of or all of the processes or in which computer readable instructions for any part of or all of the processes is stored. Non-transitory tangible computer program products are CD-ROM discs, DVD discs, flash memory, ROM cards, floppy discs, magnetic tapes, computer hard drives, and other physical storage mediums.

In view of this disclosure, instructions used in any part of or all of the processes described herein can be implemented in a wide variety of computer system configurations using an operating system and computer programming language of interest to the user.

The above description and the accompanying drawings that illustrate aspects and embodiments of the present inventions should not be taken as limiting—the claims define the protected inventions. Various mechanical, compositional, structural, electrical, and operational changes may be made without departing from the spirit and scope of this description and the claims. In some instances, well-known circuits, structures, and techniques have not been shown or described in detail to avoid obscuring the invention.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of the device in use or operation in addition to the position and orientation shown in the figures.

For example, if the device in the figures is turned over, elements described as "below" or "beneath" other elements or features would then be "above" or "over" the other elements or features. Thus, the exemplary term "below" can encompass both positions and orientations of above and below. The device may be otherwise oriented (rotated 90 degrees or at other orientations) and the spatially relative descriptors used herein interpreted accordingly.

Likewise, descriptions of movement along and around various axes include various special device positions and orientations. The singular forms "a", "an", and "the" are intended to include the plural forms as well, unless the context indicates otherwise. The terms "comprises", "comprising", "includes", and the like specify the presence of stated features, steps, operations, elements, and/or components but do not preclude the presence or addition of one or more other features, steps, operations, elements, components, and/or groups.

Components described as coupled may be electrically or mechanically directly coupled, or they may be indirectly coupled via one or more intermediate components. In view of this disclosure, instructions used in any one of, or any combination of operations described with respect to the augmented display system can be implemented in a wide variety of computer system configurations using an operating system and computer programming language of interest to the user.

All examples and illustrative references are non-limiting and should not be used to limit the claims to specific implementations and embodiments described herein and their equivalents. The headings are solely for formatting and should not be used to limit the subject matter in any way, because text under one heading may cross reference or apply to text under one or more headings. Finally, in view of this disclosure, particular features described in relation to one aspect or embodiment may be applied to other disclosed aspects or embodiments of the invention, even though not specifically shown in the drawings or described in the text.

We claim:

1. A teleoperated surgical system comprising:
an illuminator having an output optical power;
a camera; and
a controller communicatively coupled to the illuminator and to the camera and configured to maintain a target brightness of a displayed scene, the displayed scene being a scene in a frame in a video stream captured by the camera, the controller comprising a processor configured to implement:
an illumination controller; and
a camera control unit communicatively coupled to the illumination controller and to the camera and configured to receive the video stream from the camera, the camera control unit comprising:
a first control loop configured to automatically adjust one or both of a camera exposure time of the camera and a video pipeline gain; and
a second control loop configured to automatically configure the output optical power and the camera exposure time for a subsequently captured frame based on a value of the camera exposure time;
wherein:
the illumination controller is configured to control the output optical power from the illuminator in response to commands from the camera control unit; and
the camera control unit is configured to command the illumination controller to change the output optical power from a first output optical power to a second output optical power and is configured to command the camera to change a camera exposure time from a first exposure time to a second exposure time so that the subsequently captured frame is captured by the camera with the second exposure time and from reflected light, the reflected light being light from the illuminator having the second output optical power prior to being reflected.

2. The teleoperated surgical system of claim 1, wherein the camera control unit further comprises:
a statistics module coupled to the camera to receive the video stream, the statistics module being configured to create a brightness histogram for a frame in the video stream.

3. The teleoperated surgical system of claim 2, wherein:
the camera control unit further comprises:
an auto-exposure module coupled to the statistics module;

the auto-exposure module is configured to maintain the target brightness of the displayed scene;

the auto-exposure module is configured to limit saturated pixels in scenes of captured frames of the video stream to less than a predetermined number of pixels in each of the scenes; and the auto-exposure module is configured to maintain a minimum output optical power from the illuminator.

4. The teleoperated surgical system of claim 3, further comprising a high power mode switch coupled to the auto-exposure module.

5. The teleoperated surgical system of claim 2, wherein the camera control unit further comprises:

an auto-exposure module coupled to the statistics module to receive the brightness histogram for the frame in the video stream, the auto-exposure module being configured to determine an average brightness of the brightness histogram, and the auto-exposure module being configured to adjust one or both of the video pipeline gain and the camera exposure time based on a relation of the average brightness of the brightness histogram to a target brightness.

6. The teleoperated surgical system of claim 5, wherein the auto-exposure module is further configured to command the illumination controller to change the first output optical power to the second output optical power and to command the camera to adjust the camera exposure time to compensate for the change in illuminator output.

7. The teleoperated surgical system of claim 1, wherein:

the second control loop increases the output optical power and decreases the camera exposure time if the camera exposure time is larger than a first exposure threshold;

the second control loop decreases the output optical power and increases the camera exposure time if the camera exposure time is smaller than a second exposure threshold; and the second control loop leaves the output optical power and the camera exposure time unchanged if the camera exposure time is between the first exposure threshold and the second exposure threshold.

8. The teleoperated surgical system of claim 1, wherein the camera control unit further comprises:

a third control loop configured to automatically adjust the target brightness of the displayed scene to reduce a number of saturated pixels in the subsequently captured frame, the third control loop being configured to apply a range-constrained reduction to the target brightness.

9. The teleoperated surgical system of claim 1, wherein the camera control unit further comprises:

an auto-exposure module, the auto-exposure module comprising the first control loop and the second control loop.

10. The teleoperated surgical system of claim 1, wherein the camera control unit is configured to attach metadata to each frame in the video stream, the metadata proving information for pipeline synchronization.

11. The teleoperated surgical system of claim 1, wherein:

the camera control unit is configured to detect contact of an endoscope with tissue; and the camera control unit is configured to command the illumination controller to attenuate the output optical power following the contact being detected.

12. The teleoperated surgical system of claim 11, wherein the camera control unit further comprises:

a statistics module coupled to the camera to receive a scene captured by the camera, the statistics module configured to determine an overall brightness of the captured scene.

13. The teleoperated surgical system of claim 12, wherein the camera control unit further comprises:

a contact detection module coupled to the statistics module to receive the overall brightness of the captured scene, coupled to receive a camera exposure time, and coupled to the illumination controller, wherein the contact detection module is configured to detect contact of a tip of the endoscope with the tissue.

14. The teleoperated surgical system of claim 13, wherein the contact detection module is further configured to:

monitor reflected luminance; and monitor the output optical power from the illuminator.

15. The teleoperated surgical system of claim 13, wherein the contact detection module is further configured to:

determine that the endoscope tip contacted the tissue if the change from the first output optical power to the second output optical power does not result in a change of a reflected luminance for the second output optical power compared to a reflected luminance for the first output optical power.

16. The teleoperated surgical system of claim 13, wherein the illumination controller further comprises:

a dither module coupled to the contact detection module, the dither module being configured to vary the output optical power in a known pattern following being enabled by the contact detection module.

17. A teleoperated surgical system comprising:

a controller configured to maintain a target brightness of a displayed scene, the displayed scene being a scene in a frame in a video stream captured by a camera of the teleoperated surgical system, the controller comprising a processor configured to implement a camera control unit and an illumination controller, wherein:

the illumination controller is configured to control output optical power from an illuminator of the teleoperated surgical system in response to commands from the camera control unit; and the camera control unit is communicatively coupled to the illumination controller and configured to receive the video stream from the camera, and the camera control unit comprises:

a first control loop configured to automatically adjust one or both of a camera exposure time of the camera and a video pipeline gain; and a second control loop configured to automatically configure the output optical power and the camera exposure time for a subsequently captured frame based on a value of the camera exposure time; and the camera control unit is configured to command the illumination controller to change the output optical power from a first output optical power to a second output optical power and is configured to command the camera to change the camera exposure time from a first exposure time to a second exposure time so that a subsequently captured frame is captured by the camera with the second exposure time and from reflected light, the reflected light being light from the illuminator having the second output optical power prior to being reflected.

18. A teleoperated surgical system comprising:
an illuminator having an output optical power;
a camera configured to capture a scene including tissue; and
a controller coupled to the illuminator and to the camera, the controller being configured to:
- change the output optical power of the illuminator from a first output optical power to a second output optical power and change a camera exposure time from a first exposure time to a second exposure time so that a subsequently captured frame is captured by the camera with the second exposure time and from reflected light, the reflected light being light from the illuminator having the second output optical power prior to being reflected;
- determine that an endoscope contacted the tissue if a change of the output optical power of the illuminator from the first output optical power to the second output optical power does not result in a change of a reflected luminance for the second output optical power compared to a reflected luminance for the first output optical power; and
- attenuate the output optical power in response to the determination that the endoscope contacted the tissue.

* * * * *